United States Patent [19]
Karrer

[11] Patent Number: 5,648,494
[45] Date of Patent: Jul. 15, 1997

[54] CARBAMIC ACID DERIVATIVES

[75] Inventor: Friedrich Karrer, Zofingen, Switzerland

[73] Assignee: Ciba-Geigy Corporation, Tarrytown, N.Y.

[21] Appl. No.: 458,926

[22] Filed: Jun. 2, 1995

Related U.S. Application Data

[62] Division of Ser. No. 342,489, Nov. 21, 1994, abandoned, which is a division of Ser. No. 199,917, Feb. 22, 1994, Pat. No. 5,393,885, which is a division of Ser. No. 103,650, Aug. 9, 1993, abandoned.

[30] Foreign Application Priority Data

Aug. 20, 1992 [CH] Switzerland .................. 2590/92

[51] Int. Cl.$^6$ .................. C07D 211/00; C07D 207/00; C07C 271/10
[52] U.S. Cl. .................. 546/194; 548/124; 548/579; 560/164
[58] Field of Search .................. 548/124, 579; 546/194; 560/164

[56] References Cited

U.S. PATENT DOCUMENTS 4,060,629  11/1977  Karrer .
4,625,048  11/1986  Zurfluh .

FOREIGN PATENT DOCUMENTS 0169169  1/1986  European Pat. Off. .
0331529  9/1989  European Pat. Off. .
0460472  11/1991  European Pat. Off. .
2637395  2/1977  France .
2084574  4/1982  United Kingdom .

OTHER PUBLICATIONS

Brighton Crop Protection Conference, Pests & Diseases, vol. 3, 1992, pp. 1187–1192.
Brighton Crop Protection Conference, Pests & Diseases, vol. 1, 1992, pp. 43–50.

*Primary Examiner*—Joseph Conrad
*Attorney, Agent, or Firm*—Marla Mathias; William A. Teoli, Jr.

[57] ABSTRACT

Compounds of the formula

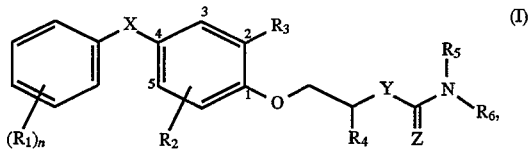

in which $R_1$ is halogen, $C_1$–$C_3$alkyl, halo-$C_1$–$C_3$alkyl, $C_1$–$C_3$alkoxy, halo-$C_1$–$C_3$alkoxy or cyano and/or two substituents $R_1$ which are bonded to adjacent C atoms of the phenyl ring together are —O—CH$_2$—O—; $R_2$ is hydrogen, halogen or methyl;

$R_3$ is fluorine, chlorine, bromine or $C_1$–$C_3$alkyl; $R_4$ is hydrogen or $C_1$–$C_3$alkyl; either $R_5$ is hydrogen, $C_1$–$C_4$alkyl,

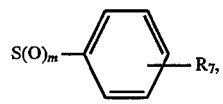

—COCO—$R_8$, —CO—$R_9$ or S(O)$_m$—N(R$_{10}$)—COO—$R_{11}$ and $R_6$ is $C_1$–$C_6$alkyl, halo-$C_1$–$C_4$alkyl, $C_2$–$C_6$alkenyl, halo-$C_3$–$C_4$alkenyl, $C_3$$C_5$alkynyl, halo-$C_3$–$C_5$alkynyl, $C_1$–$C_3$alkoxy-$C_1$–$C_3$alkyl, $C_3$–$C_6$cycloalkyl, unsubstituted or substituted phenyl; or $R_5$ and $R_6$ together are —(CH$_2$)$_4$— or —(CH$_2$)$_5$—; $R_7$ is hydrogen, halogen or $C_1$–$C_3$alkyl; $R_8$ is $C_1$–$C_8$alkoxy or —N(R$_{12}$)$_2$;

$R_9$ is $C_1$–$C_4$alkyl, $C_3$–$C_6$cycloalkyl, —N(R$_{13}$)$_2$ or $C_1$–$C_4$alkoxy;

$R_{10}$ is $C_1$–$C_3$alkyl; $R_{11}$ is $C_1$–$C_6$alkyl;

$R_{12}$ radicals independently of one another are $C_1$–$C_8$alkyl;

$R_{13}$ radicals independently of one another are $C_1$–$C_4$alkyl;

m is the number 0, 1 or 2; n is the number 0, 1, 2 or 3 where, if n is 2 or 3, the radicals $R_1$ can be identical or different; X is O, S, CH$_2$, CO or —O—CH$_2$—;

Y is O or S; and Z is O or S, with the exception of 1-(2-fluoro-4-phenoxyphenoxy)-2-ethylaminocarbonyloxyethane, in free form or in salt form, can be used as agrochemical active ingredients and can be prepared in a manner known per se.

19 Claims, No Drawings

CARBAMIC ACID DERIVATIVES

This is a divisional of Ser. No. 08/342,489, filed Nov. 21, 1994, now abandoned which is a divisional of 08/199,917, filed Feb. 22, 1994, now U.S. Pat. No. 5,393,885, which is a divisional of 08/103,650, filed Aug. 9, 1993, now abandoned.

The invention relates to compounds of the formula

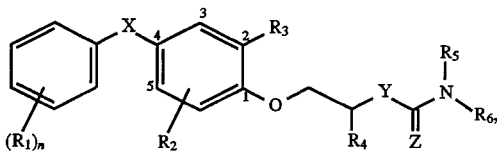

in which
$R_1$ is halogen, $C_1$–$C_3$alkyl, halo-$C_1$–$C_3$alkyl, $C_1$–$C_3$alkoxy, halo-$C_1$–$C_3$alkoxy or cyano and/or two substituents $R_1$ which are bonded to adjacent C atoms of the phenyl ring together are —O—$CH_2$—O—;

$R_2$ is hydrogen, halogen or methyl;

$R_3$ is fluorine, chlorine, bromine or $C_1$–$C_3$alkyl;

$R_4$ is hydrogen or $C_1$–$C_3$alkyl;

either $R_5$ is hydrogen, $C_1$–$C_4$alkyl,

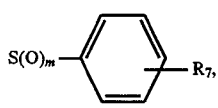

—COCO—$R_8$, —CO—$R_9$ or $S(O)_m$—$N(R_{10})$—COO—$R_{11}$ and $R_6$ is $C_1$–$C_6$alkyl, halo-$C_1$–$C_4$alkyl, $C_2$–$C_6$alkenyl, halo-$C_3$–$C_4$alkenyl, $C_3$–$C_5$alkynyl, halo-$C_3$–$C_5$alkynyl, $C_1$–$C_3$alkoxy-$C_1$–$C_3$alkyl, $C_3$–$C_6$cycloalkyl, unsubstituted phenyl or phenyl which is monosubstituted to trisubstituted by identical or different substituents selected from the group consisting of halogen, $C_1$–$C_4$alkyl and $C_1$–$C_4$alkoxy;

or $R_5$ and $R_6$ together are —$(CH_2)_4$— or —$(CH_2)_5$—;

$R_7$ is hydrogen, halogen or $C_1$–$C_3$alkyl;

$R_8$ is $C_1$–$C_8$alkoxy or —$N(R_{12})_2$;

$R_9$ is $C_1$–$C_4$alkyl, $C_3$–$C_6$cycloalkyl, —$N(R_{13})_2$ or $C_1$–$C_4$alkoxy;

$R_{10}$ is $C_1$–$C_3$alkyl;

$R_{11}$ is $C_1$–$C_6$alkyl;

$R_{12}$ radicals independently of one another are $C_1$–$C_8$alkyl;

$R_{13}$ radicals independently of one another are $C_1$–$C_4$alkyl;

m is the number 0, 1 or 2;

n is the number 0, 1, 2 or 3 where, if n is 2 or 3, the radicals $R_1$ can be identical or different;

X is O, S, $CH_2$, CO or —O—$CH_2$;

Y is O or S; and

Z is O or S, with the exception of 1-(2-fluoro-4-phenoxyphenoxy)-2-ethylaminocarbonyloxyethane, in each case in free form or in salt form, to a process for the preparation and to the use of these compounds, to pesticides whose active ingredient is selected from these compounds, in free form or in agrochemically utilizable salt form, to a process for the preparation of these compositions, to plant propagation material treated with these compositions, to a method for controlling pests, to intermediates, in free form or in salt form, for the preparation of these compounds and to a process for the preparation of these intermediates.

Certain carbamic acid derivatives are proposed in the literature as active ingredients in pesticides. However, the biological properties of these known compounds are not entirely satisfactory in the field of pest control, which is why there is a demand for providing other compounds which have pesticidal properties, in particular for controlling insects and representatives of the order of the Acarina, this object being achieved according to the invention by providing the present compounds of the formula I.

Compounds of the formula I which have at least one basic centre can form acid addition salts. These are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substituted, $C_1$–$C_4$alkanecarboxylic acids, for example acetic acid, such as unsaturated or saturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as unsubstituted or substituted, for example halogen-substituted, $C_1$–$C_4$alkane- or arylsulfonic acids, for example methane- or p-toluenesulfonic acid. Compounds I which have at least one acidic group can form salts with bases. Suitable salts with bases are, for example, metal salts, such as alkali metal salts or alkaline earth metal salts, for example sodium salts, potassium salts or magnesium salts, or salts with ammonia or an organic amine, such as morpholin, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Furthermore, corresponding internal salts can be formed, if appropriate. Preferred salts within the scope of the invention are agrochemically advantageous salts; however, the invention also embraces salts which are disadvantageous for agrochemical purposes, for example salts which are used for the isolation or purification of free compounds of the formula I or agrochemically utilizable salts thereof. The term "compounds of the formula I" hereinabove and hereinafter is thus to be understood as meaning both the free compounds of the formula I and the salts thereof.

Unless otherwise defined, the general terms used hereinabove and hereinbelow are as defined below.

Halogen—as a substituent per se and as structural element of other groups and compounds, such as haloalkyl, haloalkoxy, haloalkenyl and haloalkynyl—is fluorine, chlorine, bromine or iodine, in particular fluorine, chlorine or bromine, especially fluorine or chlorine.

Carbon-containing groups and compounds contain, unless otherwise defined, in each case 1 up to and including 8, preferably 1 up to and including 4, especially 1 up to and including 3, in particular 1 or 2, carbon atoms.

Cycloalkyl is cyclopropyl, cyclobutyl, cyclopentyl or cyclohexyl.

Alkyl—as a group per se and as structural element of other groups and compounds, such as haloalkyl, alkoxy, haloalkoxy and alkoxyalkyl—is, in each case with due consideration of the number of carbon compounds contained in each individual case in the relevant group or compound, either straight-chain, i.e. methyl, ethyl, propyl, butyl, pentyl, hexyl, heptyl or octyl, or branched, for example isopropyl, isobutyl, sec-butyl, tert-butyl, isopentyl, neopentyl, isohexyl or isooctyl.

Alkenyl and alkynyl—as groups per se and as structural elements of other groups and compounds, such as haloalkenyl and haloalkynyl—are straight-chain or branched and contain in each case two or, preferably, one unsaturated carbon-carbon bond(s). Examples which may be mentioned are vinyl, prop-1-en-3-yl, 2-methylprop-1-en-3-yl, but-2-en-1-yl, but-2-en-3-yl, prop-1-yn-3-yl, but-2-yn-1-yl and but-3-yn-1-yl.

Halogen-substituted carbon-containing groups and compounds, such as haloalkyl, haloalkoxy, haloalkenyl and haloalkynyl, can be partially halogenated or perhalogenated, where, in the case of multiple halogenation, the halogen substituents can be identical or different. Examples of haloalkyl—as a group per se and as structural element of other groups and compounds, such as haloalkoxy—are methyl which is mono- to trisubstituted by fluorine, chlorine and/or bromine, such as $CHF_2$, $CHCl_2$, $CH_2Cl$ or $CH_3$; ethyl which is mono- to pentasubstituted by fluorine, chlorine and/or bromine, such as $CH_2CH_2Cl$, $CH_2CH_2F$, $CHClCH_3$, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, each of which is mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$ or $CH(CF_3)_2$; and butyl or an isomer thereof, each of which is mono- to nonasubstituted by fluorine, chlorine and/or bromine, such as $CF(CH_3)CHFCF_3$, $CF_2(CF_2)_2CF_3$ or $CH_2(CF_2)_2CF_3$. Examples of haloalkenyl are 1-chloroprop-1-en-3-yl, 2-chloroprop-1-en-3-yl, 2,3-dibromoprop-1-en-3-yl, $CH_2CH=CHCH_2Cl$, $CH_2CH=CHCH_2F$ and $CH_2CH=CHCHF_2$. Examples of haloalkynyl are 2-chloroprop-1-yn-3-yl, 3,3-dichloroprop-1-yn-3-yl, 3,3-dibromoprop-1-yn-3-yl, 3-chloroprop-1-yn-3-yl, 3-fluoroprop-1-yn-3-yl and 4,4,4-trifluorobut-2-yn-1-yl.

In alkoxyalkyl, an alkyl group which is bonded to the remainder of the compound of the formula I is substituted by an alkoxy group, it being possible for both carbon chains independently of one another to be straight-chain or branched; examples are methoxymethyl, 1- and 2-methoxyethyl, 1- and 2-ethoxyethyl, ethoxymethyl, propoxymethyl, 2-methoxyprop-1-yl and 2-propoxyethyl.

Phenyl radicals are unsubstituted or can have one to three substituents which are identical or different. Examples are 4-chlorophenyl, 4-methoxyphenyl, 4-fluorophenyl, 3,4-dichlorophenyl or 3-chloro-4-methylphenyl.

Preferred embodiments within the scope of the invention, with consideration of the abovementioned proviso, are:

(1) A compound of the formula I in which $R_1$ is halogen, $C_1$–$C_3$alkyl, halo-$C_1$–$C_3$alkyl, $C_1$–$C_3$alkoxy, halo-$C_1$–$C_3$alkoxy or cyano and/or two substituents $R_1$ which are bonded to adjacent C atoms of the phenyl ring together are —O—$CH_2$—O—;

$R_2$ is hydrogen, halogen or methyl;

$R_3$ is chlorine, bromine or $C_1$–$C_3$alkyl;

$R_4$ is hydrogen or $C_1$–$C_3$alkyl;

$R_5$ is hydrogen, $C_1$–$C_4$alkyl,

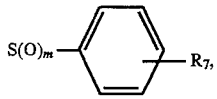

—COCO—$R_8$, —CO—$R_9$ or $S(O)_m$—N($R_{10}$)—COO—$R_{11}$;

$R_6$ is $C_1$–$C_6$alkyl; halo-$C_1$–$C_4$alkyl; $C_3$–$C_6$alkenyl, halo-$C_3$–$C_4$alkenyl,$C_3$–$C_5$alkynyl, halo-$C_3$–$C_5$alkynyl, $C_1$–$C_3$alkoxy-$C_1$–$C_3$alkyl or $C_3$–$C_6$cycloalkyl;

$R_7$ is hydrogen, halogen or $C_1$–$C_3$alkyl;

$R_8$ is $C_1$–$C_8$alkoxy or —N($R_{12}$)$_2$;

$R_9$ is $C_1$–$C_4$alkyl, $C_3$–$C_6$cycloalkyl, —N($R_{13}$)$_2$ or $C_1$C$_4$alkoxy;

$R_{10}$ is $C_1$–$C_3$alkyl;

$R_{11}$ is $C_1$–$C_6$alkyl;

$R_{12}$ radicals independently of one another are $C_1$–$C_8$alkyl;

$R_{13}$ radicals independently of one another are $C_1$–$C_4$alkyl;

m is the number 0, 1 or 2;

n is the number 0, 1, 2 or 3, where, if n is 2 or 3, the radicals $R_1$ can be identical or different;

X is O, S, $CH_2$ or CO;

Y is O or S; and

Z is O or S;

(2) A compound of the formula I in which $(R_1)_n$ is $(R_1)_0$, monofluoro, monochloro, monobromo, difluoro, dichloro, monochloromonofluoro, monobromomonofluoro, monomethyl, monoethyl, dimethyl, monomethoxy, monocyano, monotrifluoromethyl, monotrifluoromethoxy or monomethylenedioxy, in particular $(R_1)_0$, 2-, 3- or 4-fluoro, 3- or 4-chloro, 4-bromo, 2,4- or 3,5-difluoro, 3,4- or 3,5-dichloro, 3-chloro-4-fluoro, 4-bromo-2-fluoro, 3- or 4-methyl, 3- or 4-ethyl, 3,5-dimethyl, 3- or 4-methoxy, 4-cyano, 3- or 4-trifluoromethyl, 3- or 4-trifluoromethoxy or 3,4-methylenedioxy, especially $(R_1)_0$, 3- or 4-fluoro, 3-chloro, 3,5-difluoro or 3,4-dichloro, in particular $(R_1)_0$, 3-chloro or 3,5-difluoro;

(3) A compound of the formula I in which $R_2$ is hydrogen, chlorine or methyl, in particular hydrogen, 5-chloro or 5-methyl, especially hydrogen;

(4) A compound of the formula I in which $R_3$ is chlorine, bromine or methyl, in particular chlorine or bromine, especially chlorine;

(5) A compound of the formula I in which $R_3$ is fluorine;

(6) A compound of the formula I in which $R_4$ is hydrogen;

(7) A compound of the formula I in which $R_5$ is hydrogen, $C_1$–$C_4$alkyl, —S—$C_6H_4$—Cl, —COCO—$R_8$ and $R_8$ is $C_1$–$C_4$alkoxy, or $R_5$ is —CO—$R_9$ and $R_9$ is $C_1$–$C_4$alkyl, $C_1$–$C_4$alkoxy or $C_3$–$C_6$cycloalkyl, in particular in which $R_5$ is hydrogen;

(8) A compound of the formula I in which $R_6$ is $C_1$–$C_6$alkyl, halo-$C_1$–$C_3$alkyl, $C_2$–$C_4$alkenyl, halo-$C_3$–$C_4$alkenyl, $C_3$–$C_4$alkynyl, $C_1$–$C_2$alkoxy-$C_1$–$C_2$alkyl or $C_3$–$C_6$cycloalkyl, in particular $C_1$–$C_3$alkyl, halo-$C_1$–$C_2$alkyl or $C_3$–$C_4$alkenyl, especially $C_1$–$C_2$alkyl or chloro-$C_1$–$C_2$alkyl, in particular ethyl;

(9) A compound of the formula I in which $R_5$ and $R_6$ together are —$(CH_2)_4$— or —$(CH_2)_5$—;

(10) A compound of the formula I in which X is O, $CH_2$, CO or —O—$CH_2$—, especially O, $CH_2$ or CO, in particular O or $CH_2$, especially O;

(11) A compound of the formula I in which Y is O ;

(12) A compound of the formula I in which Z is O ;

(13) A compound of the formula I in which $(R_1)_n$ is $(R_1)_0$, 2-, 3- or 4-fluoro, 3- or 4-chloro, 4-bromo, 2,4- or 3,5-difluoro, 3,4- or 3,5-dichloro, 3-chloro-4-fluoro, 4-bromo-2-fluoro, 3- or 4-methyl, 3- or 4-ethyl, 3,5-dimethyl, 3- or 4-methoxy, 4-cyano, 3- or 4-trifluoromethyl, 3- or 4-trifluoromethoxy or 3,4-methylenedioxy, $R_2$ is hydrogen, chlorine or methyl, $R_3$ is fluorine, chlorine, bromine or methyl, $R_4$ is hydrogen, either $R_5$ is hydrogen, $C_1-C_4$alkyl,

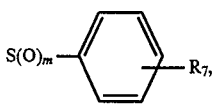

—COCO—$R_8$ or —CO—$R_9$ and $R_6$ is $C_1-C_6$alkyl, halo-$C_1-C_3$alkyl, $C_2-C_4$alkenyl, $C_3-C_4$alkynyl, $C_1-C_2$alkoxy-$C_1-C_2$alkyl or phenyl which is monosubstituted by halogen; or $R_5$ and $R_6$ together are —($CH_2$)$_4$— or —($CH_2$)$_5$—; X is O, $CH_2$, CO or —O—$CH_2$—; Y is O or S, Z is O or S, $R_7$ is hydrogen or halogen; $R_8$ is $C_1-C_4$alkoxy; $R_9$ is $C_1-C_4$alkyl or $C_3-C_6$cycloalkyl and m is 0 or 1;

(14) A compound of the formula I in which $(R_1)_n$ is $(R_1)_0$, 3- or 4-fluoro, 3-chloro, 3,5-difluoro or 3,4-dichloro, $R_2$ is hydrogen, $R_3$ is chlorine, $R_4$ is hydrogen, either $R_5$ is hydrogen and $R_6$ is $C_1-C_3$alkyl, halo-$C_1-C_2$alkyl, $C_2-C_4$alkenyl, $C_3-C_4$alkynyl, $C_1-C_2$alkoxy-$C_1-C_2$alkyl or phenyl which is monosubstituted by chlorine; or $R_5$ and $R_6$ together are —($CH_2$)$_4$—; X is O, $CH_2$, CO or —O—$CH_2$—; Y is O or S and Z is O or S;

(15) A compound of the formula I in which $(R_1)_n$ is $(R_1)_0$, $R_2$ is hydrogen, $R_3$ is fluorine, $R_4$ is hydrogen, $R_5$ is hydrogen, $R_6$ is $C_1-C_3$alkyl and X, Y and Z are in each case O;

(16) A compound of the formula I in which $(R_1)$n is $(R_1)_0$, 3-chloro or 3,5-difluoro, $R_2$ is hydrogen, $R_3$ is chlorine, $R_4$ is hydrogen, $R_5$ is hydrogen, $R_6$ is $C_1-C_2$alkyl or chloro-$C_1-C_2$alkyl and X, Y and Z are in each case O.

Particularly preferred within the scope of the invention are those compounds of the formula I which are mentioned in Examples H3 to H9.

Individually preferred within the scope of the invention are (a) 1-[2-chloro-4-(3-chlorophenoxy)phenoxy ]-2-ethylaminocarbonyloxyethane, (b) 1-(2-chloro-4-phenoxyphenoxy)-2-ethylaminocarbonyloxyethane and (c) 1-[2-chloro-4-(3,5-difluorophenoxy)phenoxy]-2-ethylaminocarbonyloxyethane.

The invention also provides a process for the preparation of the compounds of the formula I, with the exception of 1-(2-fluoro-4-phenoxyphenoxy)-2-ethylaminocarbonyloxyethane, in each case in free form or in salt form, which comprises, for example, a) reacting a compound of the formula

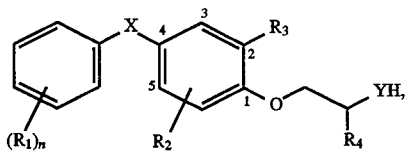

in which $R_1$, $R_2$, $R_3$, $R_4$, n, X and Y are as defined in formula I, or a salt thereof, with a compound of the formula

which is known or which can be prepared in analogy to corresponding known compounds and in which $R_5$, $R_6$ and Z are as defined in formula I and L is a leaving group, or a salt thereof, preferably in the presence of a base, or b) to prepare a compound of the formula I in which $R_5$ is hydrogen, or a salt thereof, reacting a compound of the formula (II) or a salt thereof with a compound of the formula

$R_6N=C=Z$     (IV), which is known or which can be prepared in analogy to corresponding known compounds and in which $R_6$ and Z are as defined in formula I, preferably in the presence of an acylation catalyst, or c) reacting a compound of the formula

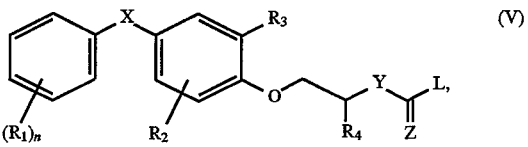

in which $R_1$, $R_2$, $R_3$, $R_4$, n, X, Y and Z are as defined in formula I and L is a leaving group, or a salt thereof, preferably in the presence of a base, with a compound of the formula

H—N($R_5$)$R_6$     (VI), which is known or which can be prepared in analogy to corresponding known compounds and in which $R_5$ and $R_6$ are as defined in formula I, or a salt thereof, or d) reacting a compound of the formula

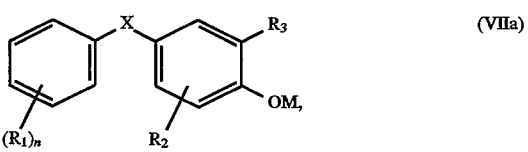

which is known or which can be prepared in analogy to corresponding known compounds and in which $R_1$, $R_2$, $R_3$, n and X are as defined in formula I and M is a cation, preferably an alkali metal ion, with a compound of the formula

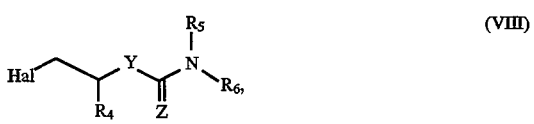

which is known or which can be prepared in analogy to corresponding known compounds and in which $R_4$, $R_5$, $R_6$, Y and Z are as defined in formula I and Hal is a halogen atom, preferably bromine, preferably in the presence of a base, and/or, if desired, convening a compound of the formula I which can be obtained according to the process or via a different route, in free form or in salt form, into a different compound of the formula I, separating an isomer mixture which can be obtained according to the process and isolating the desired isomer, and/or converting a free compound of the formula I which can be obtained according to the process or via a different route into a salt, or converting a salt of a compound of the formula I which can be obtained according to the process or via a different route into the free compound of the formula I or into a different salt.

What has been said above for salts of compounds of the formula I applies analogously to starting materials mentioned hereinabove and hereinafter with regard to the salts thereof.

The reactions described hereinabove and hereinafter are carried out in a manner known per se, for example in the absence or, conventionally, in the presence of a suitable solvent or diluent or a mixture of these, the process being carried out, as required, with cooling, at room temperature or with heating, for example in a temperature range from approximately −80° C. to the boiling point of the reaction mixture, preferably from approximately −20° C. to approximately +150° C. and, if required, in a sealed container, under elevated or reduced pressure, under an inert gas atmosphere and/or under anhydrous conditions. Particularly advantageous reaction conditions can be found in the examples.

The starting materials mentioned hereinabove and hereinafter, which are used for the preparation of the compounds of the formula I, in free form or in salt form, are known or can be prepared by methods known per se, for example following the information given below.

Variant a):

Examples of suitable leaving groups L in the compounds of the formula III are hydroxyl, $C_1$–$C_8$alkoxy, halo-$C_1$–$C_8$alkoxy, $C_1$–$C_8$alkanoyloxy, mercapto, $C_1$–$C_8$alkylthio, halo-$C_1$–$C_8$alkylthio, $C_1$–$C_8$alkanesulfonyloxy, halo-$C_1$–$C_8$alkanesulfonyloxy, benzenesulfonyloxy, toluenesulfonyloxy and halogen.

Examples of suitable bases for facilitating the detachment of HL are hydroxides, hydrides, amides, alkanolates, acetates, carbonates, dialkylamides or alkylsilylamides of alkali metals or alkaline earth metals, or alkylamines, alkylenediamines, free or N-alkylated, saturated or unsaturated, cycloalkylamines, basic heterocycles, ammonium hydroxides and carbocyclic amines. Examples which may be mentioned are sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, 4-pyrrolidin-1-ylpyridine, quinuclidine, N-methylmorpholine, benzyltrimethylammonium hydroxide and 1,5-diazabicyclo[5.4.0]undec-5-ene (DBU).

The reactants can be reacted with each other as such, i.e. without an addition of a solvent or diluent, for example in the melt. In most cases, however, the addition of an inert solvent or diluent or a mixture of these is advantageous. Examples of such solvents or diluents which may be mentioned are: aromatic, aliphatic and alicyclic hydrocarbons and halohydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric triamide; nitriles, such as acetonitrile or propionitrile; and sulfoxides, such as dimethyl sulfoxide. If the reaction is carried out in the presence of a base, then bases, such as triethylamine, pyridine, N-methylmorpholine or N,N-diethylaniline, which are employed in excess can also act as solvents or diluents.

The reaction is carried out advantageously in a temperature range from approximately −20° C. to approximately +180° C., preferably from approximately −10° C. to approximately +130° C., in many cases in the range between approximately 0° C. and the reflux temperature of the reaction mixture.

Variant b):

Examples of suitable acylation catalysts are tertiary organic bases and organotin compounds. Examples of suitable tertiary organic bases are tertiary amines and tertiary basic heterocycles, such as trimethylamine, triethylamine, diisopropylethylamine, tetramethylethylenediamine, N-cyclohexyl-N,N-dimethylamine, N,N-diethylaniline, pyridine, 4-(N,N-dimethylamino)pyridine, 4-pyrrolidin-1-ylpyridine, N-methylmorpholine, quinuclidine, 1,5-diazabicyclo[5.4.0]undec-5-ene (DBU), 1,4-diazabicyclo[2.2.2]octane and mixtures of these, and suitable organotin compounds are, for example, dialkyltin dialkanoates, such as dibutyltin diacetate.

The reactants can be reacted with each other as such, i.e. without an addition of a solvent or diluent, for example in the melt. In most cases, however, the addition of an inert solvent or diluent or a mixture of these is advantageous. Examples of such solvents or diluents which may be mentioned are: aromatic, aliphatic and alicyclic hydrocarbons and halohydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphoroic triamide; nitriles, such as acetonitrile or propionitrile; and sulfoxides, such as dimethyl sulfoxide. If the reaction is carried out in the presence of a tertiary organic base, then bases, such as triethylamine, pyridine, N-methylmorpholine or N,N-diethylaniline, which are employed in excess can also act as solvents or diluents.

The reaction is carried out advantageously in a temperature range from approximately −20° C. to approximately +180° C., preferably from approximately −10° C. to approximately +130° C., in many cases in the range between approximately 0° C. and the reflux temperature of the reaction mixture.

In a preferred embodiment of variant b), the process is carried out in the presence of an acylation catalyst, for example a trialkylamine, such as in the presence of triethylamine, and/or a bicyclic organic base, such as in the presence of 1,4-diazabicyclo[2.2.2]octane, in an ether, such as tetrahydrofuran, and at a temperature between room temperature and 80° C.

Variant c):

Suitable leaving groups L in the compounds V are, for example, of the type defined in variant a).

Suitable bases for facilitating the detachment of HL are, for example, of the type defined in variant a).

The reactants can be reacted with each other as such, i.e. without an addition of a solvent or diluent, for example in the melt. In most cases, however, the addition of an inert solvent or diluent or a mixture of these is advantageous. Suitable solvents or diluents are, for example, of the type defined in variant a).

The reaction is carried out advantageously in a temperature range from approximately −20° C. to approximately +180° C., preferably from approximately −10° C. to approximately +130° C., in many cases in the range between approximately 0° C. and the reflux temperature of the reaction mixture.

Variant d):

Examples of suitable cations in the compounds of the formula VIIa are cations of alkali metals and alkaline earth metals, preferably of alkali metals, in particular sodium ions and potassium ions.

Suitable bases for the formation of a compound of the formula VIIa from a compound of the formula

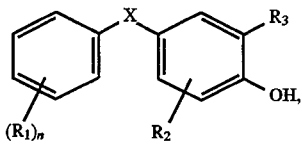 (VIIb)

which is known or which can be prepared in analogy to corresponding known compounds and in which $R_1$, $R_2$, $R_3$, n and X are as defined in formula I, are, for example, of the type defined in variant a), particularly suitable bases being sodium hydroxide, sodium hydride, sodium amide, sodium methanolate, sodium acetate, sodium carbonate, potassium tert-butanolate, potassium hydroxide, potassium carbonate, potassium hydride, lithium diisopropylamide, potassium bis (trimethylsilyl)amide, calcium hydride, particularly preferably sodium methanolate and potassium tert-butanolate. It is also possible to convert a compound of the formula VIIb with a suitable base to give a salt of the formula VIIa and to process this salt in situ to give a compound of the formula I. In this case, the base is preferably employed in excess, but a stoichiometric ratio is also possible.

The reactants can be reacted with each other as such, i.e. without an addition of a solvent or diluent, for example in the melt. In most cases, however, the addition of an inert solvent or diluent or a mixture of these is advantageous. Suitable solvents or diluents are, for example, of the type defined in variant a).

The reaction is carried out advantageously in a temperature range from approximately −20° C. to approximately +180° C., preferably from approximately −10° C. to approximately +130° C., in many cases in the range between approximately 20° C. and the reflux temperature of the reaction mixture.

The compounds V, in free form or in salt form, which are employed as educts in variant c) can be prepared in analogy to known processes, for example by reacting a compound of the formula II or a salt thereof with a compound of the formula $$Z=C(L_1)L_2 \quad (IX),$$

which is known or which can be prepared in analogy to corresponding known compounds and in which Z is as defined in formula I and $L_1$ and $L_2$ independently of one another in each case are a leaving group, such leaving groups being, for example, of the type defined in variant a) for leaving groups L, the reaction preferably being carried out as described under variant a) for the reaction of a compound of the formula II with a compound of the formula III.

According to variant c), it is also possible to prepare the intermediates V, in free form on in salt form, in situ from the compounds of the formula II and IX and to react them further without isolation, i.e. as a "one-pot process", with a compound of the formula VI or a salt thereof to give the compounds of the formula I.

The compounds of the formula II which are employed as educts for the preparation of the compounds of the formula I in variants a) and b) and as educts for the preparation of the intermediates of the formula V in variant c), with the exception of 2-(2-fluoro-4-phenoxyphenoxy)ethanol, in each case in free form or in salt form, are novel and also provided by the invention. Particularly preferred within the scope of the invention are those compounds of the formula II which are mentioned in Examples H1 and H9.

The invention also provides a process for the preparation of the compounds of the formula II, with the exception of 2-(2-fluoro-4-phenoxyphenoxy)ethanol, in each case in free form or in salt form, which comprises, for example, e) reacting a compound of the formula (VIIa) or (VIIb), with a compound of the formula

 (X)

which is known or which can be prepared in analogy to corresponding known compounds and in which $R_4$ and Y are as defined in formula I, preferably in an inert solvent or diluent, for example a solvent or diluent of the type defined in variant b), and in the presence of an alkylation catalyst, for example a tertiary amine, such as in the presence of triethylamine, or f) to prepare a compound of the formula II in which $R_4$ is hydrogen and Y is O, or a salt thereof, reacting a compound of the formula (VIIa) or (VIIb) with 2-oxo-1,3-dioxolane, preferably in the melt and in the presence of an alkylation catalyst, for example a quaternary ammonium salt, such as in the presence of tetraethylammonium chloride, or g) to prepare a compound of the formula II in which $R_4$ is hydrogen and Y is O, or a salt thereof, reacting a compound of the formula

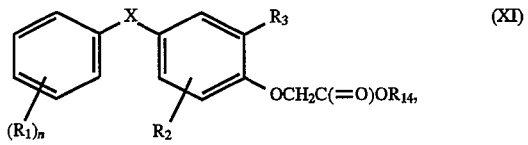 (XI)

which is known or which can be prepared in analogy to corresponding known compounds and in which $R_1$, $R_2$, $R_3$, n and X are as defined in formula I and $R_{14}$ is $C_1$–$C_8$alkyl, with a reducing agent, for example with a complex metal hydride, such as lithium aluminium hydride, preferably in an inert solvent or diluent, for example in an ether, such as diethyl ether or tetrahydrofuran, and/or, if desired, convening a compound of the formula II which can be obtained according to the process or via a different route, in free form or in salt form, into a different compound of the formula II, separating an isomer mixture which can be obtained according to the process and isolating the desired isomer, and/or converting a free compound of the formula II which can be obtained according to the process or via a different route into a salt, or converting a salt of a compound of the formula II which can be obtained according to the process or via a different route into the free compound of the formula II or into a different salt.

A compound of the formula I or II which can be obtained according to the process or via a different route can be converted in a manner known per se into a different compound of the formula I or II by replacing one or more substituents of the starting compound of the formula I or II in the customary manner by (a) different substituent(s) according to the invention.

For example, in the compounds of the formula I, hydrogen substituents $R_5$ can be exchanged for alkyl, mercapto, sulfinyl, sulfonyl or carbonyl groups $R_5$;

in the compounds of the formula I, mercapto groups $R_5$ can be oxidized to sulfinyl or sulfonyl groups $R_5$ or sulfinyl groups $R_5$ can be oxidized to sulfonyl groups $R_5$; or compounds of the formula II in which Y is O can be converted into compounds of the formula II in which Y is S.

Depending on the choice of the reaction conditions and starting materials suitable in each case, it is possible to replace, in one reaction step, only one substituent by a different substituent according to the invention, or a plurality of substituents can be replaced by different substituents according to the invention in the same reaction step.

Salts of compounds of the formula I or II can be prepared in a manner known per se. For example, acid addition salts of compounds of the formula I or II are obtained by treating them with a suitable acid or a suitable ion-exchanger reagent, and salts with bases are obtained by treating them with a suitable base or a suitable ion-exchanger reagent.

Salts of compounds of the formula I or II can be converted in the customary manner into the free compounds of the formula I or II, for example acid addition salts by treating them with a suitable base or a suitable ion-exchanger reagent and salts with bases for example by treating them with a suitable acid or a suitable ion-exchanger reagent.

Salts of compounds of the formula I or II can be convened in a manner known per se to give different salts of compounds of the formula I or II, for example acid addition salts can be converted into different acid addition salts, for example by treating a salt of an inorganic acid, such as a hydrochloride, with a suitable metal salt, such as a sodium salt, barium salt or silver salt, of an acid, for example with silver acetate, in a suitable solvent in which an inorganic salt which forms, for example silver chloride, is insoluble and so precipitates from the reaction mixture.

Depending on the procedure or the reaction conditions, the compounds of the formula I or II which have salt-forming properties can be obtained in free form or in the form of salts.

The compounds of the formula I or II, in free form or in salt form, can be present in the form of one of the isomers which are possible or in the form of a mixture of these, for example, depending on the number, absolute and relative configuration of asymmetric carbon atoms in the molecule and/or depending on the configuration of non-aromatic double bonds which occur in the molecule, in the form of pure isomers, such as antipodes and/or diastereomers, or in the form of isomer mixtures, such as enantiomer mixtures, for example racemates, diastereomer mixtures or racemate mixtures; the invention relates both to the pure isomers and to all isomer mixtures which are possible and is hereinabove and hereinafter in each case to be understood accordingly, even though stereochemical details are not mentioned specifically in each case.

Diastereomer mixtures and racemate mixtures of compounds of the formula I or II, in free form or in salt form, which can be obtained according to the process—depending on the choice of the starting substances and procedures—or via other routes can be resolved on the basis of the physico-chemical differences of the components in a known manner to give the pure diastereomers or racemates, for example by fractional crystallization, distillation and/or chromatography.

Enantiomer mixtures which can be obtained accordingly, such as racemates, can be resolved by known methods to give the optical antipodes, for example by recrystallization from an optically active solvent, by chromatography on chiral adsorbents, for example high-pressure liquid chromatography (HPLC) on acetylcellulose, with the aid of suitable microorganisms, by cleavage with specific, immobilized enzymes, via the formation of inclusion compounds, for example using chiral crown ethers which complex only one enantiomer, or by conversion into diastereomeric salts, for example by reacting a basic end product racemate with an optically active acid, such as a carboxylic acid, for example camphoric acid, tartaric acid or malic acid, or a sulfonic acid, for example camphorsulfonic acid, and resolving the resulting diastereomer mixture, for example by fractional crystallization due to the differing solubilities, to give the diastereomers from which the desired enantiomer can be freed by allowing suitable agents, for example bases to react on them.

Pure diastereomers and enantiomer can be obtained according to the invention not only by resolving suitable isomer mixtures but also by generally known methods of diastereoselective synthesis and enantioselective synthesis, respectively, for example by carrying out the process according to the invention with educts with the appropriate, suitable stereochemistry.

If the individual components differ with regard to their biological activity, it is advantageous to isolate, or synthesize, in each case the biologically more effective isomer, for example enantiomer or diastereomer, or isomer mixture, for example enantiomer mixture or diastereomer mixture.

The compounds of the formula I and II, in free form or in salt form, can also be obtained in the form of their hydrates and/or include other solvents, for example solvents used, if desired, for crystallizing compounds which are in solid form.

The invention relates to all those embodiments of the process in which, starting with a compound which can be obtained in any step of the process is used as starting material intermediate, all or some of the missing steps are carried out, or a starting material in the form of a derivative or salt and/or the racemates or antipodes thereof is used or, in particular, formed under the reaction conditions.

It is preferred to use those starting materials and intermediates, in each case in free form or in salt form, in the process of the present invention which give the compounds of the formula I, or salts thereof, which have been described at the outset as being particularly valuable.

In particular, the invention relates to the preparation processes described in Examples H 1 to H8.

The invention also provides starting materials and intermediates, in each case in free form or in salt form, which are novel and used according to the invention for the preparation of the compounds of the formula I or the salts thereof, a process for their preparation, and their use as starting materials and intermediates for the preparation of the compounds of the formula I; in particular, this applies to the compounds of the formula II.

The compounds of the formula I according to the invention are valuable as preventive and/or curative active ingredients in the field of pest control, even at low rates of concentration, and have a highly favourable biocidal spectrum while being well tolerated by warm-blooded species, fish and plants. The active ingredients according to the invention are active against all or individual development stages of normally sensitive, but also resistant, animal pests, such as insects and representatives of the order Acarina. The insecticidal and/or acaricidal activity of the active ingredients according to the invention can become apparent, for example, either directly from a destruction of the pests which occurs either immediately or only after some time has elapsed, for example during moulting, or indirectly, for example from reduced oviposition and/or hatching rates, the good activity corresponding to a mortality rate of not less than 50 to 60 %.

The abovementioned animal pests include, for example: from the order Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., Busseola fusca, *Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

from the order Coleoptera, for example

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Oryzaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example

Blatta spp., Blattella spp., Gryllotalpa spp., *Leucophaea maderae*, Locusta spp., Periplaneta spp. and Schistocerca spp.;

from the order Isoptera, for example

Reticulitermes spp.;

from the order Psocoptera, for example

Liposcelis spp.;

from the order Anoplura, for example

Haematopinus spp., Linognathus spp., Pediculus spp., Pemphigus spp. and Phylloxera spp.;

from the order Mallophaga, for example

Damalinea spp. and Trichodectes spp.;

from the order Thysanoptera, for example

Frankliniella spp., Hercinothrips spp., Taeniothrips spp., *Thrips palmi, Thrips tabaci* and *Scirtothrips aurantii;* from the order Heteroptera, for example

Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

from the order Homoptera, for example

*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma lanigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example

Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

from the order Diptera, for example

Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

from the order Siphonaptera, for example

Ceratophyllus spp. and *Xenopsylla cheopis;* from the order Thysanura, for example

*Lepisma saccharina* and from the order Acarina, for example *Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp..

The active ingredients according to the invention allow pests of the abovementioned type which can be found, in particular, on plants, especially useful plants and ornamentals, in agriculture, horticulture and silviculture, or on parts of such plants, such as fruits, flowers, foliage, stalks, tubers or roots, to be controlled, i.e. contained or destroyed, and in some cases the protection against these pests extends to parts of plants which are formed at a later point in time.

Target crops which are possible are, in particular, cereals, such as wheat, barley, rye, oats, rice, maize or sorghum; beet, such as sugar beet or fodder beet; fruit, for example pome fruit, stone fruit and soft fruit, such as apples, pears, plums, peaches, almonds, cherries or berries, for example strawberries, raspberries or blackberries; leguminous plants, such as beans, lentils, peas or soya beans; oil crops, such as oilseed rape, mustard, poppies, olives, sunflowers, coconuts, castor, cocoa or groundnuts; curcurbits, such as pumpkins, cucumbers or melons; fibre plants, such as cotton, flax, hemp or jute; citrus fruits, such as oranges, lemons, grapefruit or tangerines; vegetables, such as spinach, lettuce, asparagus, cabbages, carrots, onions, tomatoes, potatoes or bell peppers; Lauraceae, such as avocado, cinnamon or camphor; and tobacco, nuts, coffee, eggplants, sugar cane, tea, pepper, vines, hops, Musaceae, latex plants and ornamentals.

The active ingredients according to the invention are particularly suitable for controlling *Adoxophyes reticulana, Cydia pomonella, Heliothis virescens, Lobesia botrane* and *Nilaparvata lugens* in citrus, fruit and rice crops.

Other fields in which the active ingredients according to the invention can be applied are the protection of stored products and stores, the protection of material and, in the hygiene sector, in particular the protection of domestic animals and productive livestock against pests of the abovementioned type.

The invention therefore also relates to pesticides such as emulsifable concentrates, suspension concentrates, ready-to-spray or ready-to-dilute solutions, spreadable pastes, dilute emulsions, wettable powders, soluble powders, dispersible powders, dusts, granules or encapsulations in polymeric substances which are to be chosen depending on the intended aims and the prevailing circumstances and comprise—at least—one of the active ingredients according to the invention.

In these compositions, the active ingredient is employed as pure active ingredient, for example a solid active ingredient in a specific particle size or, preferably, together with—at least—one of the auxiliaries conventionally used in the art of formulation, such as extenders, for example solvents or solid carriers, or such as surface-active compounds (surfactants).

The following are examples of suitable solvents: partially hydrogenated or unhydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and their ethers and esters, such as propylene glycol, dipropylene glycol ether, ethylene glycol, ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, or water, epoxidized and unexpoxidized vegetable oils, such as epoxidized and unexpoxidized rapeseed oil, castor oil, coconut oil or soya oil, and silicone oils.

Solid carriers which are used, for example, for dusts and dispersible powders are, as a rule, natural ground minerals, such as calcite, talc, kaolin, montmorillonite or attapulgite. To improve the physical properties, it is also possible to add highly-disperse silicas or highly-disperse absorptive polymers. Possible particulate, adsorptive carriers for granules are either porous types, for example pumice, brick grit, sepiolite or bentonite, or non-sorptive carrier materials, for example calcite or sand. Moreover, a large number of granulated materials of inorganic or organic nature can be used in particular dolomite or comminuted plant residues.

Suitable surface-active compounds are non-ionic, cationic and/or anionic surfactants or surfactant mixtures which have good emulsifying, dispersing and wetting properties, depending on the nature of the active ingredient to be formulated. The surfactants listed hereinbelow are only to be regarded as examples; a large number of other surfactants conventionally used in the art of formulation and suitable according to the invention are described in the specialist literature.

Suitable non-ionic surfactants are mainly polyglycol ether derivatives of aliphatic or cycloaliphatic alcohols, saturated or unsaturated fatty acids and alkylphenols, which can have 3 to 30 glycol ether groups and 8 to 20 carbon atoms in the (aliphatic) hydrocarbon radical and 6 to 18 carbon atoms in the alkyl radical of the alkylphenols. Other suitable non-ionic surfactants are water-soluble polyethylene oxide adducts with polypropylene glycol, ethylene diaminopolypropylene glycol and alkyl polypropylene glycol which have 1 to 10 carbon atoms in the alkyl chain and 20 to 250 ethylene glycol ether groups and 10 to 100 propylene glycol ether groups. The abovementioned compounds customarily have 1 to 5 ethylene glycol units per propylene glycol unit. Examples which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Other substances which are suitable are fatty acid esters of polyoxyethylene sorbitan, such as polyoxyethylene sorbitan trioleate.

The cationic surfactants am mainly quaternary ammonium salts which have, as substituents, at least one alkyl radical having 8 to 22 carbon atoms and, as further substituents, lower, halogenated or unhalogenated alkyl, benzyl or lower hydroxyalkyl radicals. The salts are preferably in the form of halides, methylsulfates or ethylsulfates. Examples are stearyltrimethylammonium chloride and benzyldi(2-chloroethyl)ethylammonium bromide.

Suitable anionic surfactants can be either water-soluble soaps or water-soluble, synthetic surface-active compounds. Soaps which are suitable are the alkali metal salts, alkaline earth metal salts and substituted or unsubstituted ammonium salts of higher fatty acids ($C_{10}$–$C_{22}$), such as the sodium salts or potassium salts of oleic or stearic acid, or of natural mixtures of fatty acids which can be obtained from, for example, coconut oil or tall oil; the fatty acid methyltaurinates must also be mentioned. However, synthetic surfactants are used more frequently, in particular fatty sulfonates, fatty sulfates, sulfonated benzimidazole derivatives or alkylarylsulfonates. The fatty sulfonates and fatty sulfates are, as a rule, in the form of alkali metal salts, alkaline earth metal salts or substituted or unsubstituted ammonium salts and have, as a rule, an alkyl radical having 8 to 22 carbon atoms, alkyl also including the alkyl moiety of acyl radicals, for example the sodium salt or calcium salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives have preferably 2 sulfonyl groups and a fatty acid radical having approximately 8 to 22 carbon atoms. Alkylarylsulfonates are, for example, the sodium salts, calcium salts or triethanolamine salts of dodecylbenzenesulfonic acid, of dibutylnaphthalenesulfonic acid or of a naphthalenesulfonic acid/formaldehyde condensation product. Suitable phosphates, such as salts of the phosphoric ester of a p-nonylphenol/(4-14)ethylene oxide adduct, or phospholipids, are also suitable.

As a rule, the compositions comprise 0.1 to 99%, in particular 0.1 to 95%, of active ingredient and 1 to 99.9%, in particular 5 to 99.9%, of—at least—one solid or liquid auxiliary, it being possible, as a rule, for 0 to 25%, in particular 0. 1 to 20%, of the compositions to be surfactants (% in each case meaning per cent by weight). While concentrated compositions are more preferred as commercially available goods, the end consumer uses, as a rule, dilute compositions with considerably lower concentrations of active ingredients. Preferred compositions are, in particular, composed as follows (% =per cent by weight):

| Emulsifiable concentrates: | | |
|---|---|---|
| Active ingredient | 1 to 90%, | preferably 5 to 20% |
| Surfactant: | 1 to 30%, | preferably 10 to 20% |
| Solvent: | 5 to 98%, | preferably 70 to 85% |
| Dusts: | | |
| Active ingredient: | 0.1 to 10%, | preferably 0.1 to 1% |
| Solid carrier: | 99.9 to 90%, | preferably 99.9 to 99% |
| Suspension concentrates: | | |
| Active ingredient: | 5 to 75%, | preferably 10 to 50% |
| Water: | 94 to 24%, | preferably 88 to 30% |
| Surfactant: | 1 to 40%, | preferably 2 to 30% |
| Wettable powders: | | |
| Active ingredient: | 0.5 to 90%, | preferably 1 to 80% |
| Surfactant: | 0.5 to 20%, | preferably 1 to 15% |
| Solid carrier: | 5 to 99%, | preferably 15 to 98% |
| Granules: | | |
| Active ingredient: | 0.5 to 30%, | preferably 3 to 15% |
| Solid carrier: | 99.5 to 70%, | preferably 97 to 85% |

The activity of the compositions according to the invention can be widened considerably and adapted to prevailing circumstances by adding other insecticidal and/or acaricidal active ingredients. Representatives of the following active ingredient classes are examples of suitable additions of active ingredients: organophosphorus compounds, nitrophenols and derivatives, formamidines, ureas, carbamates, pyrethroids, chlorinated hydrocarbons and *Bacillus thuringiensis* preparations. The compositions according to the invention can also comprise other solid or liquid auxiliaries such as stabilizers, for example epoxidized or unepoxidized vegetable oils (for example epoxidized coconut oil, rapeseed oil or soya oil), antifoams, for example silicone oil, preservatives, viscosity regulators, binders and/or tackifiers, and also fertilizers or other active ingredients for achieving specific effects, for example bactericides, fungicides, nematicides, molluscicides or selective herbicides.

The compositions according to the invention are prepared in a known manner; in the absence of auxiliaries, for example, by grinding, screening and/or compressing of a solid active ingredient or active ingredient mixture, for example to give a certain particle size, and in the presence of at least one auxiliary, for example, by intimately mixing and/or grinding the active ingredient or active ingredient mixture with the auxiliary or auxiliaries. The invention also provides these processes for the preparation of the compositions according to the invention and the use of the compounds of the formula I for the preparation of these compositions.

The invention also provides the methods of application for the compositions, i.e. the methods for controlling pests of the abovementioned type, such as spraying, atomizing, dusting, painting on, seed-dressing, scattering or pouring, depending on the intended aims and the prevailing circumstances, and the use of the compositions for controlling pests of the abovementioned type. Typical rates of application are between 0.1 and 1000 ppm, preferably between 0.1 and 500 ppm, of active ingredient. The rates of application per hectare are, as a rule, 1 to 2000 g of active ingredient per hectare, in particular 10 to 1000 g/ha, preferably 20 to 600 g/ha.

A preferred method of application in the field of crop protection is application to the foliage of the plants (foliar application), where frequency and rate of application will depend on the risk of infestation with the pest in question. However, the active ingredient can also reach the plants via the root system (systemic action) by drenching the locus of the plants with a liquid composition or incorporating the active ingredient into the locus of the plants, for example into the soil, in solid form, for example in the form of granules (soil application). In crops of paddy rice, such granules can be metered into the flooded paddy field.

The compositions according to the invention are also suitable for protecting plant propagation material, for example seed, such as fruits, tubers or kernels, or plant cuttings, against animal pests. The propagation material can be treated with the composition before planting, for example seed can be dressed before sowing. The active ingredients according to the invention can also be applied to seed kernels (coating) either by soaking the kernels in a liquid composition or by applying a layer of a solid composition. The composition can also be applied to the site of application when the propagation material is planted, for example when it is sown into the seed furrow. The invention also provides these treatment methods for plant propagation material and the plant propagation material which has been treated in this manner.

The examples which follow are intended to illustrate the invention. They do not impose any limitation. Temperatures are given in degrees centigrade, mixing ratios of solvents in parts by volume.

Preparation examples

EXAMPLE H1

2-[12-Chloro-4-(3-chlorophenoxy)phenoxy]ethanol (Compound No. 10.1.6).

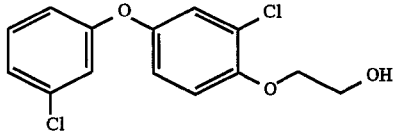

A mixture of 7.7 g of 2-chloro-4-(3-chlorophenoxy) phenol, 3.17 g of 2-oxo-1,3-dioxolane and 1.3 g of tetraethylammonium chloride is molten together, the melt is heated at 130° C. for 8 hours with stirring under a nitrogen atmosphere; after cooling, the reaction mixture is taken up in 150 g of diethyl ether, and the ether phase is washed several times with water, dried over sodium sulfate and evaporated to dryness. The residue is purified by chromatography [silica gel; diethyl ether/hexane (1:1)]. This gives the title compound which has a refractive index $n_D^{20}$ of 1.5995.

EXAMPLE H2

2-(2-Chloro-4-phenoxy)phenoxyethyl chlorocarbonate

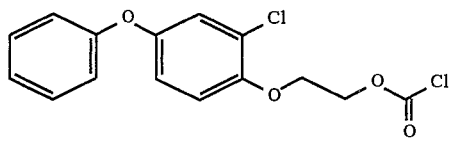

19.8 g of phosgene are passed in the course of 2 to 3 hours into a mixture of 39.7 g of 2-(2-chloro-4-phenoxy)phenoxyethanol in 150 ml of toluene at 55° C., with stirring. Stirring is continued for 14 hours at 50° C. The solvent is removed on a rotary evaporator and the residue is recrystallized from n-hexane. This gives the title product of melting point 84°–85.5° C.

EXAMPLE H3

1-[2-Chloro-4-(3-chlorophenoxy)phenoxy]-2-ethylaminocarbonyloxyethane (Table 1, Compound No. 1.2.6).

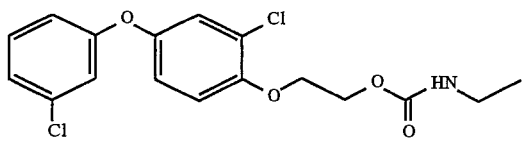

0.1 ml of triethylamine, 15 mg of 1,4-diazabicyclo[2.2.2]octane and 1.3 g of ethyl isocyanate are added to a solution of 4.49 g of 2-[2-chloro-4-(3-chlorophenoxy)phenoxy] ethanol in 40 ml of tetrahydrofuran. The reaction mixture is heated at 55° for 18 hours, with stirring, and then evaporated to dryness in vacuo. The residue is purified by chromatography [silica gel; diethyl ether/hexane (2:3)]. This gives the title compound which melts at 73°–74° C.

EXAMPLE H4

1-[2-Chloro-4-(4-fluorophenoxy)phenoxy]-2-ethylaminocarbonyloxyethane (Compound 1.2.4).

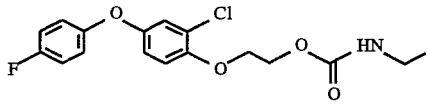

A solution of 1.41 g of potassium tert-butylate in 20 ml of dimethyl sulfoxide is added dropwise with stirring at 10°–15° C. to 2.86 g of 2-chloro-4-(4-fluorophenoxy)phenol in 10 ml of dimethyl sulfoxide. 2.92 g of 2-bromoethyl ethylcarbamate in 10 ml of dimethyl sulfoxide are subsequently added dropwise at room temperature and the mixture is then stirred for 18 hours at 40° C. The reaction mixture is then poured into 300 ml of ice-water and extracted several times using ether. The combined ether phases are washed to neutrality using a small amount of water and dried over sodium sulfate and the solvent is evaporated in vacuo. The crude product is purified on silica gel using diethyl ether/hexane (1:9) as eluent. This gives the title compound of melting point 42°–43° C.

EXAMPLE H5

1-[2-Chloro-4-phenoxyphenoxy]-2-N-pyrrolidinocarbonyloxyethane (Compound 1.121.1)

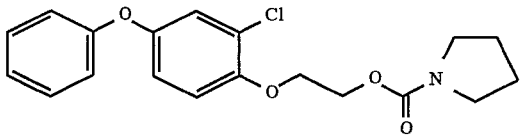

A solution of 4 g of 2-(2-chloro-4-phenoxy)phenoxyethyl chlorocarbonate in 20 ml of dichloromethane is added dropwise with stirring at 5°–10° C. to a mixture of 2.2 g of pyrrolidine in 20 ml of dichloromethane. After stirring has been continued for three hours at room temperature, the reaction mixture is washed three times using 50 ml portions of 1N hydrochloric acid and then three times using water and dried over sodium sulfate and the solvent is evaporated. The residue is stirred with n-hexane, filtered and washed with cold hexane. This gives the title compound of melting point 79°–81° C.

EXAMPLE H6

1-[2-Chloro-4-phenoxyphenoxy]-2-[N-(4-chlorophenyl)aminocarbonyloxy]ethane (Compound 1.124.1)

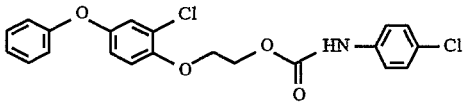

4 g of 2-(2-chloro-4-phenoxy)phenoxyethyl chlorocarbonate in 20 ml of dichloromethane are added dropwise with stirring at 5°–10° C. to 3.95 g of 4-chloroaniline in 20 ml of dichloromethane. After the reaction mixture has been stirred for two hours at room temperature, 100 ml of dichloromethane am added and the mixture is washed three times using 1N hydrochloric acid and three times using water. The organic phase is dried over sodium sulfate and the solvent is evaporated in vacuo. The crude product is stirred with n-hexane, filtered and washed with cold hexane. This gives the title compound of melting point 155°–155.5° C.

EXAMPLE H7

1-[2-Chloro-4-(3-chlorophenoxy)phenoxy]-2-[N-ethyl-N-(4-chlorophenylsulfenyl)aminocarbonyloxy]ethane (Compound 1.68.6)

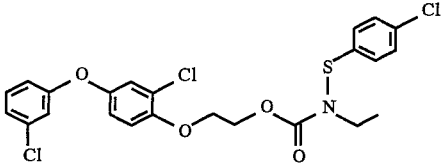

A solution of 2 g of 4-chlorophenylsulfenyl chloride in 10 ml of toluene is added dropwise with stirring at 0°–5° C. in the course of approximately 30 minutes to a mixture of 3.7 g of 1-[2-chloro-4-(3-chlorophenoxy)phenoxy]2-ethylaminocarbonyloxyethane, 10 ml of pyridine and 10 ml of toluene, and stirring is continued for 16 hours at room temperature. The reaction mixture is diluted with 100 ml of ether, washed three times using ice-cold 1N hydrochloric acid and three times using water, the organic phase is dried over sodium sulfate and the solvent is evaporated in vacuo. The crude product is purified on silica gel using diethyl ether/n-hexane (1:3) as mobile phase. This gives the title compound of refractive index $n^D_{20} 1.6209$.

EXAMPLE H8

1-[2-Chloro-4-(3-chlorophenoxy)phenoxy]-2-(N-ethyl-N-acetylaminocarbonyloxy)ethane (Compound 1.80.6)

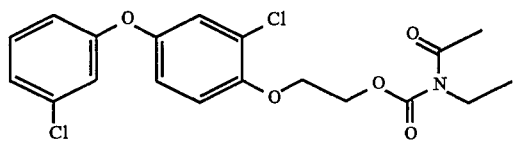

4.7 g of acetyl chloride are added dropwise at 10°–20° C. to a mixture of 5.55 g of 1-[2-chloro-4-(3-chlorophenoxy) phenoxy]-2-ethylaminocarbonyloxyethane, 3.6 g of pyridine, 0.15 g of dimethylaminopyridine and 60 ml of toluene. The mixture is then stirred for 50 hours at reflux temperature. The batch is poured into 300 ml of ice-water and is extracted three times using diethyl ether. The combined ether phases are washed using 1N hydrochloric acid and three times using water, dried over sodium sulfate and the solvent is evaporated in vacuo. The crude product is purified on silica gel using diethyl ether/n-hexane (2:7) as mobile phase. This gives the title compound of refractive index $n^D_{20} 1.5640$.

EXAMPLE H9

The other compounds listed in Tables 1 to 14 can also be prepared as described in Examples H1 to H8. In Tables 7, 8, 9, 13 and 14, each line discloses exactly one compound of a particular constitution. In contrast, in Tables 1 to 6 and 10 to 12, each individual line discloses not only one single compound of a particular constitution. Rather, in the column "Compounds" of these tables, the term "1-2", "1-7" and "1-26", which in each line occupies the space after the second dot in this column, is used to denote, by means of the number which follows the hyphen, how many compounds of different constitution are disclosed by the line in question. Accordingly, the term "1-2" is used to denote that the line in question discloses two individual compounds of different constitution. For example, the line in Table 5 which starts "5.1.1-2" discloses the two compounds 5.1.1 and 5.1.2, which differ from each other with regard to their constitution, while the term "4.2.1-7" denotes the seven compounds 4.2.1, 4.2.2, . . . , 4.2.6 and 4.2.7, all of which differ from each other with regard to their constitution, and the term "1.8.1-26" denotes the 26 compounds 1.8.1, 1.8.2, . . . , 1.8.25 and 1.8.26, all of which differ from each other with regard to their constitution. Each of the individual compounds disclosed in the line in question differ from each other with regard to their constitution only in such a way that in each of them the variable $(R_1)_n$ has a different meaning. Each number in the term "1-2" (1 to 2), i.e. 1 and 2, each number in the term "1-7" (1 to 7), i.e. 1,2 . . . , 6 and 7, and each number in the term "1-26" (1 to 26), i.e. 1, 2, . . . , 25 and 26, has in each case a certain meaning of $(R_1)_n$ which is the same in all lines of all Tables 1 to 6 and 9 to 11, namely 1 in the case of $(R_1)_0$, 2 in 4-chloro, 3 in 3-fluoro, 4 in 4-fluoro, 5 in 3,5-difluoro, 6 in 3-chloro, 7 in 3,4-dichloro, 8 in 2-fluoro, 9 in 3,5-dichloro, 10 in 3-chloro-4-fluoro, 11 in 2,4-difluoro, 12 in 4-bromo-2-fluoro, 13 in 4-bromo, 14 in 3-methyl, 15 in 4methyl, 16 in 3-ethyl, 17 in 4-ethyl, 18 in 4-cyano, 19 in 3-trifluoromethyl, 20 in 3,5-dimethyl, 21 in 4-trifluoromethyl, 22 in 3-methoxy, 23 in 4-methoxy, 24 in 3,4-methylenedioxy, 25 in 3-trifluoromethoxy and 26 in 4-trifluoromethoxy. Thus, a particular choice of the number after the second dot in the column "Compounds" in conjunction with the meanings of the remaining variables given in the line in question results in an unequivocal allocation of a certain compound number to one single compound whose constitution is defined and where all variables including $(RI)_n$ have a particular meaning. For example, the compound 3.78.23 is the compound of the formula I in which $R_1$ is 4-methoxy, $R_2$ is hydrogen, $R_3$ is chlorine, $R_4$ is hydrogen, $R_5$ is $COCON(C_4H_9)_2$, $R_6$ is ethyl, n is 1, X is methylene, Y is O and Z is O, and the compound 12.14.2 is the compound of the formula II in which $R_1$ is 4-chloro, $R_2$ is 5-methyl, $R_3$ is methyl, $R_4$ is hydrogen, n is 1, X is C(=O) and Y is O. The temperatures given in the column "Physical data" of Table 14 denote in each case the melting point of the compound in question, and "$n_D^T$" is the refractive index of the compound in question at a temperature of T° C.

TABLE 1

| Compounds | $R_2$ | $R_3$ | $R_4$ | $R_5$ | $R_6$ |
|---|---|---|---|---|---|
| 1.1.1-26 | H | Cl | H | H | $CH_3$ |
| 1.2.1-26 | H | Cl | H | H | $C_2H_5$ |
| 1.3.1-26 | H | Cl | H | H | $n-C_3H_7$ |
| 1.4.1-26 | H | Cl | H | H | $i-C_3H_7$ |
| 1.5.1-26 | H | Cl | H | H | $n-C_4H_9$ |
| 1.6.1-26 | H | Cl | H | H | $i-C_4H_9$ |
| 1.7.1-26 | H | Cl | H | H | $s-C_4H_9$ |
| 1.8.1-26 | H | Cl | H | H | $t-C_4H_9$ |
| 1.9.1-26 | H | Cl | H | H | $CH_2CH_2Cl$ |
| 1.10.1-26 | H | Cl | H | H | $CH_2CH_2F$ |
| 1.11.1-26 | H | Cl | H | H | $CH_2CH=CH_2$ |
| 1.12.1-26 | H | Cl | H | H | $CH_2C\equiv CH$ |
| 1.13.1-26 | H | Cl | H | H | $cis-CH_2CH=CHCl$ |

TABLE 1-continued

| Compounds | $R_2$ | $R_3$ | $R_4$ | $R_5$ | $R_6$ |
|---|---|---|---|---|---|
| 1.14.1-26 | H | Cl | H | H | $CH_2CCl=CH_2$ |
| 1.15.1-26 | H | Cl | H | H | cis-$CH_2CH=CHCH_3$ |
| 1.16.1-26 | H | Cl | H | H | $CHClCH_3$ |
| 1.17.1-26 | H | Cl | H | H | $CH_2CF_3$ |
| 1.18.1-26 | H | Cl | H | H | $CH_2CF_2CF_3$ |
| 1.19.1-26 | H | Cl | H | H | c-$C_3H_5$ |
| 1.20.1-26 | H | Cl | H | H | c-$C_5H_9$ |
| 1.21.1-26 | H | Cl | H | H | c-$C_6H_{11}$ |
| 1.22.1-26 | H | Cl | H | H | $CH_2CH_2OCH_3$ |
| 1.23.1-26 | H | Cl | H | H | $CH_2CH_2OC_2H_5$ |
| 1.24.1-26 | H | Cl | H | H | $CH_2C(CH_3)=CH_2$ |
| 1.25.1-26 | H | Br | H | H | $CH_3$ |
| 1.26.1-26 | H | Br | H | H | $C_2H_5$ |
| 1.27.1-26 | H | Br | H | H | i-$C_3H_7$ |
| 1.28.1-26 | H | Br | H | H | $C_3H_7$ |
| 1.29.1-26 | H | Br | H | H | $CH_2CH_2Cl$ |
| 1.30.1-26 | H | Br | H | H | $CH_2CH_2F$ |
| 1.31.1-26 | H | Cl | H | H | trans-$CH_2CH=CHCl$ |
| 1.32.1-26 | H | Br | $CH_3$ | H | $C_2H_5$ |
| 1.33.1-26 | H | Br | $C_2H_5$ | H | $C_2H_5$ |
| 1.34.1-26 | H | Br | $C_3H_7$ | H | $C_2H_5$ |
| 1.35.1-26 | 5-Cl | Br | H | H | $C_2H_5$ |
| 1.36.1-26 | 5-$CH_3$ | Br | H | H | $C_2H_5$ |
| 1.37.1-26 | H | Br | H | $CH_3$ | $CH_3$ |
| 1.38.1-26 | H | Br | H | $C_2H_5$ | $CH_3$ |
| 1.39.1-26 | H | Br | H | $C_2H_5$ | $C_2H_5$ |
| 1.40.1-26 | H | Br | H | S—$C_6H_5$ | $C_2H_5$ |
| 1.41.1-26 | H | Br | H | S—$C_6H_4$-4-Cl | $C_2H_5$ |
| 1.42.1-26 | H | Br | H | S—$C_6H_4$-4-Br | $C_2H_5$ |
| 1.43.1-26 | H | Br | H | S—$C_6H_4$-4-$CH_3$ | $C_2H_5$ |
| 1.44.1-26 | H | Br | H | S—$C_6H_4$-2-Cl | $C_2H_5$ |
| 1.45.1-26 | H | Br | H | $S(=O)$—$C_6H_5$ | $C_2H_5$ |
| 1.46.1-26 | H | Br | H | $S(=O)_2$—$C_6H_5$ | $C_2H_5$ |
| 1.47.1-26 | H | Br | H | $COCOOCH_3$ | $C_2H_5$ |
| 1.48.1-26 | H | Br | H | $COCOOC_2H_5$ | $CH_3$ |
| 1.49.1-26 | H | Br | H | $COCOOC_2H_5$ | $C_2H_5$ |
| 1.50.1-26 | H | Br | H | $COCON(C_2H_5)_2$ | $C_2H_5$ |
| 1.51.1-26 | H | Br | H | $COC_2H_5$ | $CH_3$ |
| 1.52.1-26 | H | Br | H | $COCH_3$ | $C_2H_5$ |
| 1.53.1-26 | H | Br | H | $COC_2H_5$ | $C_2H_5$ |
| 1.54.1-26 | H | Br | H | CO-i-$C_3H_7$ | $C_2H_5$ |
| 1.55.1-26 | H | Br | H | CO-c-$C_3H_5$ | $C_2H_5$ |
| 1.56.1-26 | H | Br | H | $COOCH_3$ | $C_2H_5$ |
| 1.57.1-26 | H | Br | H | $COOC_2H_5$ | $C_2H_5$ |
| 1.58.1-26 | 5-$CH_3$ | Cl | H | H | $C_2H_5$ |
| 1.59.1-26 | 5-Cl | Cl | H | H | $C_2H_5$ |
| 1.60.1-26 | H | Cl | $CH_3$ | H | $C_2H_5$ |
| 1.61.1-26 | H | Cl | $C_2H_5$ | H | $C_2H_5$ |
| 1.62.1-26 | H | Cl | H | $CH_3$ | $C_2H_5$ |
| 1.63.1-26 | H | Cl | H | $C_2H_5$ | $C_2H_5$ |
| 1.64.1-26 | H | Cl | H | i-$C_3H_7$ | $C_2H_5$ |
| 1.65.1-26 | H | Cl | H | $C_3H_7$ | $C_2H_5$ |
| 1.66.1-26 | H | Cl | H | S—$C_6H_5$ | $CH_3$ |
| 1.67.1-26 | H | Cl | H | S—$C_6H_5$ | $C_2H_5$ |
| 1.68.1-26 | H | Cl | H | S—$C_6H_4$-4-Cl | $C_2H_5$ |
| 1.69.1-26 | H | Cl | H | S—$C_6H_4$-4-Br | $C_2H_5$ |
| 1.70.1-26 | H | Cl | H | S—$C_6H_4$-4-$CH_3$ | $C_2H_5$ |
| 1.71.1-26 | H | Cl | H | $S(=O)$—$C_6H_5$ | $C_2H_5$ |
| 1.72.1-26 | H | Cl | H | $S(=O)_2$—$C_6H_5$ | $C_2H_5$ |
| 1.73.1-26 | H | Cl | H | $COCOOC_2H_5$ | $CH_3$ |
| 1.74.1-26 | H | Cl | H | $COCOOCH_3$ | $C_2H_5$ |
| 1.75.1-26 | H | Cl | H | $COCOOC_2H_5$ | $C_2H_5$ |
| 1.76.1-26 | H | Cl | H | $COCON(CH_3)_2$ | $C_2H_5$ |
| 1.77.1-26 | H | Cl | H | $COCON(C_2H_5)_2$ | $C_2H_5$ |
| 1.78.1-26 | H | Cl | H | $COCON(C_4H_9)_2$ | $C_2H_5$ |
| 1.79.1-26 | H | Cl | H | $COC_2H_5$ | $CH_3$ |
| 1.80.1-26 | H | Cl | H | $COCH_3$ | $C_2H_5$ |
| 1.81.1-26 | H | Cl | H | $COC_2H_5$ | $C_2H_5$ |
| 1.82.1-26 | H | Cl | H | CO-i-$C_3H_7$ | $C_2H_5$ |

TABLE 1-continued

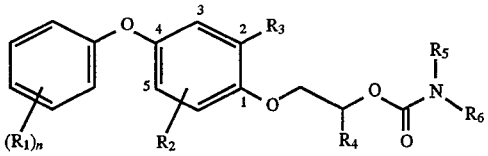

| Compounds | R₂ | R₃ | R₄ | R₅ | R₆ |
|---|---|---|---|---|---|
| 1.83.1-26 | H | Cl | H | CO-c-$C_3H_5$ | $C_2H_5$ |
| 1.84.1-26 | H | Cl | H | COOCH₃ | $C_2H_5$ |
| 1.85.1-26 | H | Cl | H | COOC₂H₅ | $C_2H_5$ |
| 1.86.1-26 | H | Cl | H | COOC₃H₇ | $C_2H_5$ |
| 1.87.1-26 | H | Cl | H | COCOOC₈H₁₇ | $C_2H_5$ |
| 1.88.1-26 | H | Cl | H | COC₃H₇ | $C_2H_5$ |
| 1.89.1-26 | H | Cl | H | CO-c-C₅H₉ | $C_2H_5$ |
| 1.90.1-26 | H | CH₃ | H | H | CH₃ |
| 1.91.1-26 | H | CH₃ | H | H | $C_2H_5$ |
| 1.92.1-26 | H | CH₃ | H | H | CH₂CH₂Cl |
| 1.93.1-26 | H | CH₃ | H | H | CHClCH₃ |
| 1.94.1-26 | H | CH₃ | H | H | CH₂CH₂F |
| 1.95.1-26 | H | CH₃ | H | H | n-C₃H₇ |
| 1.96.1-26 | H | CH₃ | H | H | i-C₃H₇ |
| 1.97.1-26 | H | Cl | H | H | trans-CH₂CH=CHCH₃ |
| 1.98.1-26 | H | CH₃ | CH₃ | H | $C_2H_5$ |
| 1.99.1-26 | H | CH₃ | H | CH₃ | $C_2H_5$ |
| 1.100.1-26 | H | CH₃ | H | $C_2H_5$ | $C_2H_5$ |
| 1.101.1-26 | H | CH₃ | H | S—C₆H₅ | $C_2H_5$ |
| 1.102.1-26 | H | CH₃ | H | S—C₆H₄-4-Cl | $C_2H_5$ |
| 1.103.1-26 | H | CH₃ | H | S—C₆H₄-4-Br | $C_2H_5$ |
| 1.104.1-26 | H | CH₃ | H | S—C₆H₄-4-CH₃ | $C_2H_5$ |
| 1.105.1-26 | H | CH₃ | H | S—C₆H₄-2-Cl | $C_2H_5$ |
| 1.106.1-26 | H | CH₃ | H | COCOOCH₃ | $C_2H_5$ |
| 1.107.1-26 | H | CH₃ | H | COCOOC₂H₅ | $C_2H_5$ |
| 1.108.1-26 | H | CH₃ | H | COCON(C₂H₅)₂ | $C_2H_5$ |
| 1.109.1-26 | H | CH₃ | H | COCH₃ | $C_2H_5$ |
| 1.110.1-26 | H | CH₃ | H | COC₂H₅ | $C_2H_5$ |
| 1.111.1-26 | H | CH₃ | H | COC₃H₇ | $C_2H_5$ |
| 1.112.1-26 | H | CH₃ | H | CO-i-C₃H₇ | $C_2H_5$ |
| 1.113.1-26 | H | CH₃ | H | CO-c-C₃H₅ | $C_2H_5$ |
| 1.114.1-26 | H | Cl | H | H | C₆H₁₃ |
| 1.115.1-26 | 5-CH₃ | CH₃ | H | H | $C_2H_5$ |
| 1.116.1-26 | 5-Cl | CH₃ | H | H | $C_2H_5$ |
| 1.117.1-26 | H | Cl | H | COC₄H₉ | $C_2H_5$ |
| 1.118.1-26 | H | Cl | H | COOC₄H₉ | $C_2H_5$ |
| 1.119.1-26 | H | Cl | H | S—N(CH₃)COOC₄H₉ | $C_2H_5$ |
| 1.120.1-26 | H | CH₃ | H | C₄H₉ | $C_2H_5$ |
| 1.121.1-26 | H | Cl | H | —(CH₂)₄— | |
| 1.122.1-26 | H | Cl | H | H | —CH=CH₂ |
| 1.123.1-26 | H | Cl | H | H | —C₆H₅ |
| 1.124.1-26 | H | Cl | H | H | —C₆H₄-4-Cl |
| 1.125.1-26 | H | Cl | H | CH₃ | CH₃ |
| 1.126.1-26 | H | F | H | H | CH₃ |
| 1.127.2-26 | H | F | H | H | $C_2H_5$ |
| 1.128.1-26 | H | F | H | H | n-C₃H₇ |
| 1.129.1-26 | H | F | H | H | i-C₃H₇ |
| 1.130.1-26 | H | F | H | H | n-C₄H₉ |
| 1.131.1-26 | H | F | H | H | i-C₄H₉ |
| 1.132.1-26 | H | F | H | H | s-C₄H₉ |
| 1.133.1-26 | H | F | H | H | t-C₄H₉ |
| 1.134.1-26 | H | F | H | H | CH₂CH₂Cl |
| 1.135.1-26 | H | F | H | H | CH₂CH₂F |
| 1.136.1-26 | H | F | H | H | CH₂CH=CH₂ |
| 1.137.1-26 | H | F | H | H | CH₂C≡CH |
| 1.138.1-26 | H | F | H | H | cis-CH₂CH=CHCl |
| 1.139.1-26 | H | F | H | H | CH₂CCl=CH₂ |
| 1.140.1-26 | H | F | H | H | cis-CH₂CH=CHCH₃ |
| 1.141.1-26 | H | F | H | H | CHClCH₃ |
| 1.142.1-26 | H | F | H | H | CH₂CF₃ |
| 1.143.1-26 | H | F | H | H | CH₂CF₂CF₃ |
| 1.144.1-26 | H | F | H | H | c-C₃H₅ |
| 1.145.1-26 | H | F | H | H | c-C₅H₉ |
| 1.146.1-26 | H | F | H | H | c-C₆H₁₁ |
| 1.147.1-26 | H | F | H | H | CH₂CH₂OCH₃ |
| 1.148.1-26 | H | F | H | H | CH₂CH₂OC₂H₅ |
| 1.149.1-26 | H | F | H | H | CH₂C(CH₃)=CH₂ |
| 1.150.1-26 | H | F | $C_2H_5$ | H | $C_2H_5$ |

TABLE 1-continued

| Compounds | $R_2$ | $R_3$ | $R_4$ | $R_5$ | $R_6$ |
|---|---|---|---|---|---|
| 1.151.1-26 | H | F | H | $CH_3$ | $C_2H_5$ |
| 1.152.1-26 | H | F | H | $C_2H_5$ | $C_2H_5$ |
| 1.153.1-26 | H | F | H | i-$C_3H_7$ | $C_2H_5$ |
| 1.154.1-26 | H | F | H | $C_3H_7$ | $C_2H_5$ |
| 1.155.1-26 | H | F | H | S—$C_6H_5$ | $CH_3$ |
| 1.156.1-26 | H | F | H | S—$C_6H_5$ | $C_2H_5$ |
| 1.157.1-26 | H | F | H | S—$C_6H_4$-4-Cl | $C_2H_5$ |
| 1.158.1-26 | H | F | H | S—$C_6H_4$-4-Br | $C_2H_5$ |
| 1.159.1-26 | H | F | H | S—$C_6H_4$-4-$CH_3$ | $C_2H_5$ |
| 1.160.1-26 | H | F | H | S(=O)—$C_6H_5$ | $C_2H_5$ |
| 1.161.1-26 | H | F | H | S(=O)$_2$—$C_6H_5$ | $C_2H_5$ |
| 1.162.1-26 | H | F | H | COCOO$C_2H_5$ | $CH_3$ |
| 1.163.1-26 | H | F | H | COCOO$CH_3$ | $C_2H_5$ |
| 1.164.1-26 | H | F | H | COCOO$C_2H_5$ | $C_2H_5$ |
| 1.165.1-26 | H | F | H | COCON($CH_3$)$_2$ | $C_2H_5$ |
| 1.166.1-26 | H | F | H | COCON($C_2H_5$)$_2$ | $C_2H_5$ |
| 1.167.1-26 | H | F | H | COCON($C_4H_9$)$_2$ | $C_2H_5$ |
| 1.168.1-26 | H | F | H | CO$C_2H_5$ | $CH_3$ |
| 1.169.1-26 | H | F | H | CO$CH_3$ | $C_2H_5$ |
| 1.170.1-26 | H | F | H | CO$C_2H_5$ | $C_2H_5$ |
| 1.171.1-26 | H | F | H | CO-i-$C_3H_7$ | $C_2H_5$ |
| 1.172.1-26 | H | F | H | CO-c-$C_3H_5$ | $C_2H_5$ |
| 1.173.1-26 | H | F | H | COO$CH_3$ | $C_2H_5$ |
| 1.174.1-26 | H | F | H | COO$C_2H_5$ | $C_2H_5$ |
| 1.175.1-26 | H | F | H | COO-n-$C_3H_7$ | $C_2H_5$ |
| 1.176.1-26 | H | F | H | COCOO-n-$C_8H_{17}$ | $C_2H_5$ |
| 1.177.1-26 | H | F | H | CO-n-$C_3H_7$ | $C_2H_5$ |
| 1.178.1-26 | H | F | H | CO-c-$C_5H_9$ | $C_2H_5$ |
| 1.179.1-26 | H | F | H | —(CH$_2$)$_4$— | |
| 1.180.1-26 | H | Cl | $CH_3$ | H | $CH_3$ |
| 1.181.1-26 | H | Cl | H | CO-n-$C_3H_7$ | $C_2H_5$ |

TABLE 2

| Compounds | $R_3$ | $R_6$ | Y | Z |
|---|---|---|---|---|
| 2.1.1-26 | $CH_3$ | $C_2H_5$ | S | O |
| 2.2.1-26 | Cl | $C_2H_5$ | S | O |
| 2.3.1-26 | Cl | $C_2H_5$ | O | S |
| 2.4.1-26 | Cl | $C_2H_5$ | S | S |
| 2.5.1-26 | Cl | $CH_3$ | O | S |
| 2.6.1-26 | $CH_3$ | $C_2H_5$ | O | S |
| 2.7.1-26 | Br | $CH_3$ | O | S |
| 2.8.1-26 | Br | $C_2H_5$ | O | S |
| 2.9.1-26 | Cl | $CH_2$—CH=$CH_2$ | O | S |

TABLE 3

| Compounds | $R_2$ | $R_3$ | $R_4$ | $R_5$ | $R_6$ |
|---|---|---|---|---|---|
| 3.1.1-7 | H | Cl | H | H | $CH_3$ |
| 3.2.1-7 | H | Cl | H | H | $C_2H_5$ |
| 3.3.1-7 | H | Cl | H | H | $n-C_3H_7$ |
| 3.4.1-7 | H | Cl | H | H | $i-C_3H_7$ |
| 3.5.1-7 | H | Cl | H | H | $n-C_4H_9$ |
| 3.6.1-7 | H | Cl | H | H | $i-C_4H_9$ |
| 3.7.1-7 | H | Cl | H | H | $s-C_4H_9$ |
| 3.8.1-7 | H | Cl | H | H | $t-C_4H_9$ |
| 3.9.1-7 | H | Cl | H | H | $CH_2CH_2Cl$ |
| 3.10.1-7 | H | Cl | H | H | $CH_2CH_2F$ |
| 3.11.1-7 | H | Cl | H | H | $CH_2CH=CH_2$ |
| 3.12.1-7 | H | Cl | H | H | $CH_2C\equiv CH$ |
| 3.13.1-7 | H | Cl | H | H | $cis-CH_2CH=CHCl$ |
| 3.14.1-7 | H | Cl | H | H | $CH_2CCl=CH_2$ |
| 3.15.1-7 | H | Cl | H | H | $cis-CH_2CH=CHCH_3$ |
| 3.16.1-7 | H | Cl | H | H | $CHClCH_3$ |
| 3.17.1-7 | H | Cl | H | H | $CH_2CF_3$ |
| 3.18.1-7 | H | Cl | H | H | $CH_2CF_2CF_3$ |
| 3.19.1-7 | H | Cl | H | H | $c-C_3H_5$ |
| 3.20.1-7 | H | Cl | H | H | $c-C_5H_9$ |
| 3.21.1-7 | H | Cl | H | H | $c-C_6H_{11}$ |
| 3.22.1-7 | H | Cl | H | H | $CH_2CH_2OCH_3$ |
| 3.23.1-7 | H | Cl | H | H | $CH_2CH_2OC_2H_5$ |
| 3.24.1-7 | H | Cl | H | H | $CH_3C(CH_3)=CH_2$ |
| 3.25.1-7 | H | Br | H | H | $CH_3$ |
| 3.26.1-7 | H | Br | H | H | $C_2H_5$ |
| 3.27.1-7 | H | Br | H | H | $i-C_3H_7$ |
| 3.28.1-7 | H | Br | H | H | $C_3H_7$ |
| 3.29.1-7 | H | Br | H | H | $CH_2CH_2Cl$ |
| 3.30.1-7 | H | Br | H | H | $CH_2CH_2F$ |
| 3.31.1-7 | H | Cl | H | H | $trans-CH_2CH=CHCl$ |
| 3.32.1-7 | H | Br | $CH_3$ | H | $C_2H_5$ |
| 3.33.1-7 | H | Br | $C_2H_5$ | H | $C_2H_5$ |
| 3.34.1-7 | H | Br | $C_3H_7$ | H | $C_2H_5$ |
| 3.35.1-7 | 5-Cl | Br | H | H | $C_2H_5$ |
| 3.36.1-7 | 5-$CH_3$ | Br | H | H | $C_2H_5$ |
| 3.37.1-7 | H | Br | H | $CH_3$ | $C_2H_5$ |
| 3.38.1-7 | H | Br | H | $C_2H_5$ | $CH_3$ |
| 3.39.1-7 | H | Br | H | $C_2H_5$ | $C_2H_5$ |
| 3.40.1-7 | H | Br | H | $S-C_6H_5$ | $C_2H_5$ |
| 3.41.1-7 | H | Br | H | $S-C_6H_4-4-Cl$ | $C_2H_5$ |
| 3.42.1-7 | H | Br | H | $S-C_6H_4-4-Br$ | $C_2H_5$ |
| 3.43.1-7 | H | Br | H | $S-C_6H_4-4-CH_3$ | $C_2H_5$ |
| 3.44.1-7 | H | Br | H | $S-C_6H_4-2-Cl$ | $C_2H_5$ |
| 3.45.1-7 | H | Br | H | $S(=O)-C_6H_5$ | $C_2H_5$ |
| 3.46.1-7 | H | Br | H | $S(=O)_2-C_6H_5$ | $C_2H_5$ |
| 3.47.1-7 | H | Br | H | $COCOOCH_3$ | $C_2H_5$ |
| 3.48.1-7 | H | Br | H | $COCOOC_2H_5$ | $CH_3$ |
| 3.49.1-7 | H | Br | H | $COCOOC_2H_5$ | $C_2H_5$ |
| 3.50.1-7 | H | Br | H | $COCON(C_2H_5)_2$ | $C_2H_5$ |
| 3.51.1-7 | H | Br | H | $COC_2H_5$ | $CH_3$ |
| 3.52.1-7 | H | Br | H | $COCH_3$ | $C_2H_5$ |
| 3.53.1-7 | H | Br | H | $COC_2H_5$ | $C_2H_5$ |
| 3.54.1-7 | H | Br | H | $CO-i-C_3H_7$ | $C_2H_5$ |
| 3.55.1-7 | H | Br | H | $CO-c-C_3H_5$ | $C_2H_5$ |
| 3.56.1-7 | H | Br | H | $COOCH_3$ | $C_2H_5$ |
| 3.57.1-7 | H | Br | H | $COOC_2H_5$ | $C_2H_5$ |
| 3.58.1-7 | 5-$CH_3$ | Cl | H | H | $C_2H_5$ |
| 3.59.1-7 | 5-Cl | Cl | H | H | $C_2H_5$ |
| 3.60.1-7 | H | Cl | $CH_3$ | H | $C_2H_5$ |
| 3.61.1-7 | H | Cl | $C_2H_5$ | H | $C_2H_5$ |
| 3.62.1-7 | H | Cl | H | $CH_3$ | $C_2H_5$ |
| 3.63.1-7 | H | Cl | H | $C_2H_5$ | $C_2H_5$ |
| 3.64.1-7 | H | Cl | H | $i-C_3H_7$ | $C_2H_5$ |
| 3.65.1-7 | H | Cl | H | $C_3H_7$ | $C_2H_5$ |
| 3.66.1-7 | H | Cl | H | $S-C_6H_5$ | $CH_3$ |
| 3.67.1-7 | H | Cl | H | $S-C_6H_5$ | $C_2H_5$ |
| 3.68.1-7 | H | Cl | H | $S-C_6H_4-4-Cl$ | $C_2H_5$ |

TABLE 3-continued

| Compounds | $R_2$ | $R_3$ | $R_4$ | $R_5$ | $R_6$ |
|---|---|---|---|---|---|
| 3.69.1-7 | H | Cl | H | $S-C_6H_4-4-Br$ | $C_2H_5$ |
| 3.70.1-7 | H | Cl | H | $S-C_6H_4-4-CH_3$ | $C_2H_5$ |
| 3.71.1-7 | H | Cl | H | $S(=O)-C_6H_5$ | $C_2H_5$ |
| 3.72.1-7 | H | Cl | H | $S(=O)_2-C_6H_5$ | $C_2H_5$ |
| 3.73.1-7 | H | Cl | H | $COCOOC_2H_5$ | $CH_3$ |
| 3.74.1-7 | H | Cl | H | $COCOOCH_3$ | $C_2H_5$ |
| 3.75.1-7 | H | Cl | H | $COCOOC_2H_5$ | $C_2H_5$ |
| 3.76.1-7 | H | Cl | H | $COCON(CH_3)_2$ | $C_2H_5$ |
| 3.77.1-7 | H | Cl | H | $COCON(C_2H_5)_2$ | $C_2H_5$ |
| 3.78.1-7 | H | Cl | H | $COCON(C_4H_9)_2$ | $C_2H_5$ |
| 3.79.1-7 | H | Cl | H | $COC_2H_5$ | $CH_3$ |
| 3.80.1-7 | H | Cl | H | $COCH_3$ | $C_2H_5$ |
| 3.81.1-7 | H | Cl | H | $COC_2H_5$ | $C_2H_5$ |
| 3.82.1-7 | H | Cl | H | $CO-i-C_3H_7$ | $C_2H_5$ |
| 3.83.1-7 | H | Cl | H | $CO-c-C_3H_5$ | $C_2H_5$ |
| 3.84.1-7 | H | Cl | H | $COOCH_3$ | $C_2H_5$ |
| 3.85.1-7 | H | Cl | H | $COOC_2H_5$ | $C_2H_5$ |
| 3.86.1-7 | H | Cl | H | $COOC_3H_7$ | $C_2H_5$ |
| 3.87.1-7 | H | Cl | H | $COCOOC_8H_{17}$ | $C_2H_5$ |
| 3.88.1-7 | H | Cl | H | $COC_3H_7$ | $C_2H_5$ |
| 3.89.1-7 | H | Cl | H | $CO-c-C_5H_9$ | $C_2H_5$ |
| 3.90.1-7 | H | $CH_3$ | H | H | $CH_3$ |
| 3.91.1-7 | H | $CH_3$ | H | H | $C_2H_5$ |
| 3.92.1-7 | H | $CH_3$ | H | H | $CH_2CH_2Cl$ |
| 3.93.1-7 | H | $CH_3$ | H | H | $CHClCH_3$ |
| 3.94.1-7 | H | $CH_3$ | H | H | $CH_2CH_2F$ |
| 3.95.1-7 | H | $CH_3$ | H | H | $C_3H_7$ |
| 3.96.1-7 | H | $CH_3$ | H | H | $i-C_3H_7$ |
| 3.97.1-7 | H | Cl | H | H | $trans-CH_2CH=CHCH_3$ |
| 3.98.1-7 | H | $CH_3$ | $CH_3$ | H | $C_2H_5$ |
| 3.99.1-9 | H | $CH_3$ | H | $CH_3$ | $C_2H_5$ |
| 3.100.1-7 | H | $CH_3$ | H | $C_2H_5$ | $C_2H_5$ |
| 3.101.1-7 | H | $CH_3$ | H | $S-C_6H_5$ | $C_2H_5$ |
| 3.102.1-7 | H | $CH_3$ | H | $S-C_6H_4-4-Cl$ | $C_2H_5$ |
| 3.103.1-7 | H | $CH_3$ | H | $S-C_6H_4-4-Br$ | $C_2H_5$ |
| 3.104.1-7 | H | $CH_3$ | H | $S-C_6H_4-4-CH_3$ | $C_2H_5$ |
| 3.105.1-7 | H | $CH_3$ | H | $S-C_6H_4-2-Cl$ | $C_2H_5$ |
| 3.106.1-7 | H | $CH_3$ | H | $COCOOCH_3$ | $C_2H_5$ |
| 3.107.1-7 | H | $CH_3$ | H | $COCOOC_2H_5$ | $C_2H_5$ |
| 3.108.1-7 | H | $CH_3$ | H | $COCON(C_2H_5)_2$ | $C_2H_5$ |
| 3.109.1-7 | H | $CH_3$ | H | $COCH_3$ | $C_2H_5$ |
| 3.110.1-7 | H | $CH_3$ | H | $COC_2H_5$ | $C_2H_5$ |
| 3.111.1-7 | H | $CH_3$ | H | $COC_3H_7$ | $C_2H_5$ |
| 3.112.1-7 | H | $CH_3$ | H | $CO-i-C_3H_7$ | $C_2H_5$ |
| 3.113.1-7 | H | $CH_3$ | H | $CO-c-C_3H_5$ | $C_2H_5$ |
| 3.114.1-7 | H | Cl | H | H | $C_6H_{13}$ |
| 3.115.1-7 | $5-CH_3$ | $CH_3$ | H | H | $C_2H_5$ |
| 3.116.1-7 | $5-Cl$ | $CH_3$ | H | H | $C_2H_5$ |
| 3.117.1-7 | H | Cl | H | $COC_4H_9$ | $C_2H_5$ |
| 3.118.1-7 | H | Cl | H | $COOC_4H_9$ | $C_2H_5$ |
| 3.119.1-7 | H | Cl | H | $S-N(CH_3)COOC_4H_9$ | $C_2H_5$ |
| 3.120.1-7 | H | $CH_3$ | H | $C_4H_9$ | $C_2H_5$ |

TABLE 4

| Compounds | $R_3$ | $R_6$ | Y | Z |
|---|---|---|---|---|
| 4.1.1-7 | $CH_3$ | $C_2H_5$ | S | O |
| 4.2.1-7 | Cl | $C_2H_5$ | S | O |
| 4.3.1-7 | Cl | $C_2H_5$ | O | S |
| 4.4.1-7 | Cl | $C_2H_5$ | S | S |
| 4.5.1-7 | Cl | $CH_3$ | O | S |
| 4.6.1-7 | $CH_3$ | $C_2H_5$ | O | S |
| 4.7.1-7 | Br | $CH_3$ | O | S |
| 4.8.1-7 | Br | $C_2H_5$ | O | S |

TABLE 5

| Compounds | $R_2$ | $R_3$ | $R_4$ | $R_5$ | $R_6$ |
|---|---|---|---|---|---|
| 5.1.1-2 | H | Cl | H | H | $CH_3$ |
| 5.2.1-2 | H | Cl | H | H | $C_2H_5$ |
| 5.3.1-2 | H | Cl | H | H | $C_3H_7$ |
| 5.4.1-2 | H | Cl | H | H | $i\text{-}C_3H_7$ |
| 5.5.1-2 | H | Cl | H | H | $C_4H_9$ |
| 5.6.1-2 | H | Cl | H | H | $i\text{-}C_4H_9$ |
| 5.7.1-2 | H | Cl | H | H | $s\text{-}C_4H_9$ |
| 5.8.1-2 | H | Cl | H | H | $t\text{-}C_4H_9$ |
| 5.9.1-2 | H | Cl | H | H | $CH_2CH_2Cl$ |
| 5.10.1-2 | H | Cl | H | H | $CH_2CH_2F$ |
| 5.11.1-2 | H | Cl | H | H | $CH_2CH=CH_2$ |
| 5.12.1-2 | H | Cl | H | H | $CH_2C\equiv CH$ |
| 5.13.1-2 | H | Cl | H | H | $cis\text{-}CH_2CH=CHCl$ |
| 5.14.1-2 | H | Cl | H | H | $CH_2CCl=CH_2$ |
| 5.15.1-2 | H | Cl | H | H | $cis\text{-}CH_2CH=CHCH_3$ |
| 5.16.1-2 | H | Cl | H | H | $CHClCH_3$ |
| 5.17.1-2 | H | Cl | H | H | $CH_2CF_3$ |
| 5.18.1-2 | H | Cl | H | H | $CH_2CF_2CF_3$ |
| 5.19.1-2 | H | Cl | H | H | $c\text{-}C_3H_5$ |
| 5.20.1-2 | H | Cl | H | H | $c\text{-}C_5H_9$ |
| 5.21.1-2 | H | Cl | H | H | $c\text{-}C_6H_{11}$ |
| 5.22.1-2 | H | Cl | H | H | $CH_2CH_2OCH_3$ |
| 5.23.1-2 | H | Cl | H | H | $CH_2CH_2OC_2H_5$ |
| 5.24.1-2 | H | Cl | H | H | $CH_2C(CH_3)=CH_2$ |
| 5.25.1-2 | H | Br | H | H | $CH_3$ |
| 5.26.1-2 | H | Br | H | H | $C_2H_5$ |
| 5.27.1-2 | H | Br | H | H | $i\text{-}C_3H_7$ |
| 5.28.1-2 | H | Br | H | H | $C_3H_7$ |
| 5.29.1-2 | H | Br | H | H | $CH_2CH_2Cl$ |
| 5.30.1-2 | H | Br | H | H | $CH_2CH_2F$ |
| 5.31.1-2 | H | Cl | H | H | $trans\text{-}CH_2CH=CHCl$ |
| 5.32.1-2 | H | Br | $CH_3$ | H | $C_2H_5$ |
| 5.33.1-2 | H | Br | $C_2H_5$ | H | $C_2H_5$ |
| 5.34.1-2 | H | Br | $C_3H_7$ | H | $C_2H_5$ |
| 5.35.1-2 | 5-Cl | Br | H | H | $C_2H_5$ |
| 5.36.1-2 | 5-$CH_3$ | Br | H | H | $C_2H_5$ |
| 5.37.1-2 | H | Br | H | $CH_3$ | $C_2H_5$ |
| 5.39.1-2 | H | Br | H | $C_2H_5$ | $CH_3$ |
| 5.39.1-2 | H | Br | H | $C_2H_5$ | $C_2H_5$ |
| 5.40.1-2 | H | Br | H | $S-C_6H_5$ | $C_2H_5$ |
| 5.41.1-2 | H | Br | H | $S-C_6H_4\text{-}4\text{-}Cl$ | $C_2H_5$ |
| 5.42.1-2 | H | Br | H | $S-C_6H_4\text{-}4\text{-}Br$ | $C_2H_5$ |

TABLE 5-continued

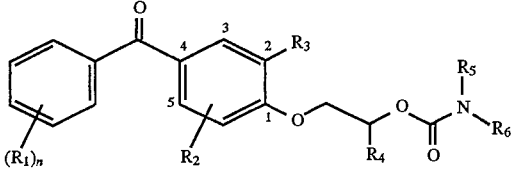

| Compounds | R₂ | R₃ | R₄ | R₅ | R₆ |
|---|---|---|---|---|---|
| 5.43.1-2 | H | Br | H | S—C₆H₄-4-CH₃ | C₂H₅ |
| 5.44.1-2 | H | Br | H | S—C₆H₄-2-Cl | C₂H₅ |
| 5.45.1-2 | H | Br | H | S(=O)—C₆H₅ | C₂H₅ |
| 5.46.1-2 | H | Br | H | S(=O)₂—C₆H₅ | C₂H₅ |
| 5.47.1-2 | H | Br | H | COCOOCH₃ | C₂H₅ |
| 5.48.1-2 | H | Br | H | COCOOC₂H₅ | CH₃ |
| 5.49.1-2 | H | Br | H | COCOOC₂H₅ | C₂H₅ |
| 5.50.1-2 | H | Br | H | COCON(C₂H₅)₂ | C₂H₅ |
| 5.51.1-2 | H | Br | H | COC₂H₅ | CH₃ |
| 5.52.1-2 | H | Br | H | COCH₃ | C₂H₅ |
| 5.53.1-2 | H | Br | H | COC₂H₅ | C₂H₅ |
| 5.54.1-2 | H | Br | H | CO-i-C₃H₇ | C₂H₅ |
| 5.55.1-2 | H | Br | H | CO-c-C₃H₅ | C₂H₅ |
| 5.56.1-2 | H | Br | H | COOCH₃ | C₂H₅ |
| 5.57.1-2 | H | Br | H | COOC₂H₅ | C₂H₅ |
| 5.58.1-2 | 5-CH₃ | Cl | H | H | C₂H₅ |
| 5.59.1-2 | 5-Cl | Cl | H | H | C₂H₅ |
| 5.60.1-2 | H | Cl | CH₃ | H | C₂H₅ |
| 5.61.1-2 | H | Cl | C₂H₅ | H | C₂H₅ |
| 5.62.1-2 | H | Cl | H | CH₃ | C₂H₅ |
| 5.63.1-2 | H | Cl | H | C₂H₅ | C₂H₅ |
| 5.64.1-2 | H | Cl | H | i-C₃H₇ | C₂H₅ |
| 5.65.1-2 | H | Cl | H | C₃H₇ | C₂H₅ |
| 5.66.1-2 | H | Cl | H | S—C₆H₅ | CH₃ |
| 5.67.1-2 | H | Cl | H | S—C₆H₅ | C₂H₅ |
| 5.68.1-2 | H | Cl | H | S—C₆H₄-4-Cl | C₂H₅ |
| 5.69.1-2 | H | Cl | H | S—C₆H₄-4-Br | C₂H₅ |
| 5.70.1-2 | H | Cl | H | S—C₆H₄-4-CH₃ | C₂H₅ |
| 5.71.1-2 | H | Cl | H | S(=O)—C₆H₅ | C₂H₅ |
| 5.72.1-2 | H | Cl | H | S(=O)₂—C₆H₅ | C₂H₅ |
| 5.73.1-2 | H | Cl | H | COCOOC₂H₅ | CH₃ |
| 5.74.1-2 | H | Cl | H | COCOOCH₃ | C₂H₅ |
| 5.75.1-2 | H | Cl | H | COCOOC₂H₅ | C₂H₅ |
| 5.76.1-2 | H | Cl | H | COCON(CH₃)₂ | C₂H₅ |
| 5.77.1-2 | H | Cl | H | COCON(C₂H₅)₂ | C₂H₅ |
| 5.78.1-2 | H | Cl | H | COCON(C₄H₉)₂ | C₂H₅ |
| 5.79.1-2 | H | Cl | H | COC₂H₅ | CH₃ |
| 5.80.1-2 | H | Cl | H | COCH₃ | C₂H₅ |
| 5.81.1-2 | H | Cl | H | COC₂H₅ | C₂H₅ |
| 5.82.1-2 | H | Cl | H | CO-i-C₃H₇ | C₂H₅ |
| 5.83.1-2 | H | Cl | H | CO-c-C₃H₅ | C₂H₅ |
| 5.84.1-2 | H | Cl | H | COOCH₃ | C₂H₅ |
| 5.85.1-2 | H | Cl | H | COOC₂H₅ | C₂H₅ |
| 5.86.1-2 | H | Cl | H | COOC₃H₇ | C₂H₅ |
| 5.87.1-2 | H | Cl | H | COCOOC₈H₁₇ | C₂H₅ |
| 5.88.1-2 | H | Cl | H | COC₃H₇ | C₂H₅ |
| 5.89.1-2 | H | Cl | H | Co-c-C₅H₉ | C₂H₅ |
| 5.90.1-2 | H | CH₃ | H | H | CH₃ |
| 5.91.1-2 | H | CH₃ | H | H | C₂H₅ |
| 5.92.1-2 | H | H | H | H | CH₂CH₂Cl |
| 5.93.1-2 | H | CH₃ | H | H | CHClCH₃ |
| 5.94.1-2 | H | CH₃ | H | H | CH₂CH₂F |
| 5.95.1-2 | H | CH₃ | H | H | C₃H₇ |
| 5.96.1-2 | H | CH₃ | H | H | i-C₃H₇ |
| 5.97.1-2 | H | Cl | H | H | trans-CH₂CH=CHCH₃ |
| 5.98.1-2 | H | CH₃ | CH₃ | H | C₂H₅ |
| 5.99.1-2 | H | CH₃ | H | CH₃ | C₂H₅ |
| 5.100.1-2 | H | CH₃ | H | C₂H₅ | C₂H₅ |
| 5.101.1-2 | H | CH₃ | H | S—C₆H₅ | C₂H₅ |
| 5.102.1-2 | H | CH₃ | H | S—C₆H₄-4-Cl | C₂H₅ |
| 5.103.1-2 | H | CH₃ | H | S—C₆H₄-4-Br | C₂H₅ |
| 5.104.1-2 | H | CH₃ | H | S—C₆H₄-4-CH₃ | C₂H₅ |
| 5.105.1-2 | H | CH₃ | H | S—C₆H₄-2-Cl | C₂H₅ |
| 5.106.1-2 | H | CH₃ | H | COCOOCH₃ | C₂H₅ |
| 5.107.1-2 | H | CH₃ | H | COCOOC₂H₅ | C₂H₅ |
| 5.108.1-2 | H | CH₃ | H | COCON(C₂H₅)₂ | C₂H₅ |
| 5.109.1-2 | H | CH₃ | H | COCH₃ | C₂H₅ |
| 5.110.1-2 | H | CH₃ | H | COC₂H₅ | C₂H₅ |

TABLE 5-continued

| Compounds | $R_2$ | $R_3$ | $R_4$ | $R_5$ | $R_6$ |
|---|---|---|---|---|---|
| 5.111.1-2 | H | $CH_3$ | H | $COC_3H_7$ | $C_2H_5$ |
| 5.112.1-2 | H | $CH_3$ | H | $CO-i-C_3H_7$ | $C_2H_5$ |
| 5.113.1-2 | H | $CH_3$ | H | $CO-c-C_3H_5$ | $C_2H_5$ |
| 5.114.1-2 | H | $CH_3$ | H | H | $C_6H_{13}$ |
| 5.115.1-2 | 5-$CH_3$ | $CH_3$ | H | H | $C_2H_5$ |
| 5.116.1-2 | 5-Cl | $CH_3$ | H | H | $C_2H_5$ |
| 5.117.1-2 | H | Cl | H | $COC_4H_9$ | $C_2H_5$ |
| 5.118.1-2 | H | Cl | H | $COOC_4H_9$ | $C_2H_5$ |
| 5.119.1-2 | H | Cl | H | $S-N(CH_3)COOC_4H_9$ | $C_2H_5$ |
| 5.120.1-2 | H | $CH_3$ | H | $C_4H_9$ | $C_2H_5$ |

TABLE 6

| Compounds | $R_3$ | $R_6$ | Y | Z |
|---|---|---|---|---|
| 6.1.1-2 | $CH_3$ | $C_2H_5$ | S | O |
| 6.2.1-2 | Cl | $C_2H_5$ | S | O |
| 6.3.1-2 | Cl | $C_2H_5$ | O | S |
| 6.4.1-2 | Cl | $C_2H_5$ | S | S |
| 6.5.1-2 | Cl | $CH_3$ | O | S |
| 6.6.1-2 | $CH_3$ | $C_2H_5$ | O | S |
| 6.7.1-2 | Br | $CH_3$ | O | S |
| 6.8.1-2 | Br | $C_2H_5$ | O | S |

TABLE 7

| Compounds | $R_2$ | $R_3$ | $R_4$ | $R_5$ | $R_6$ |
|---|---|---|---|---|---|
| 7.1 | H | Cl | H | H | $CH_3$ |
| 7.2 | H | Cl | H | H | $C_2H_5$ |
| 7.3 | H | Cl | H | H | $C_3H_7$ |
| 7.4 | H | Cl | H | H | $i-C_3H_7$ |
| 7.5 | H | Cl | H | H | $C_4H_9$ |
| 7.6 | H | Cl | H | H | $i-C_4H_9$ |
| 7.7 | H | Cl | H | H | $s-C_4H_9$ |
| 7.8 | H | Cl | H | H | $t-C_4H_9$ |
| 7.9 | H | Cl | H | H | $CH_2CH_2Cl$ |
| 7.10 | H | Cl | H | H | $CH_2CH_2F$ |
| 7.11 | H | Cl | H | H | $CH_2CH=CH_2$ |
| 7.12 | H | Cl | H | H | $CH_2C\equiv CH$ |
| 7.13 | H | Cl | H | H | cis-$CH_2CH=CHCl$ |
| 7.14 | H | Cl | H | H | $CH_2CCl=CH_2$ |

TABLE 7-continued

| Compounds | $R_2$ | $R_3$ | $R_4$ | $R_5$ | $R_6$ |
|---|---|---|---|---|---|
| 7.15 | H | Cl | H | H | cis-$CH_2CH=CHCH_3$ |
| 7.16 | H | Cl | H | H | $CHClCH_3$ |
| 7.17 | H | Cl | H | H | $CH_2CF_3$ |
| 7.18 | H | Cl | H | H | $CH_2CF_2CF_3$ |
| 7.19 | H | Cl | H | H | c-$C_3H_5$ |
| 7.20 | H | Cl | H | H | c-$C_5H_9$ |
| 7.21 | H | Cl | H | H | c-$C_6H_{11}$ |
| 7.22 | H | Cl | H | H | $CH_2CH_2OCH_3$ |
| 7.23 | H | Cl | H | H | $CH_2CH_2OC_2H_5$ |
| 7.24 | H | Cl | H | H | $CH_2C(CH_3)=CH_2$ |
| 7.25 | H | Br | H | H | $CH_3$ |
| 7.26 | H | Br | H | H | $C_2H_5$ |
| 7.27 | H | Br | H | H | i-$C_3H_7$ |
| 7.28 | H | Br | H | H | $C_3H_7$ |
| 7.29 | H | Br | H | H | $CH_2CH_2Cl$ |
| 7.30 | H | Br | H | H | $CH_2CH_2F$ |
| 7.31 | H | Cl | H | H | trans-$CH_2CH=CHCl$ |
| 7.32 | H | Br | $CH_3$ | H | $C_2H_5$ |
| 7.33 | H | Br | $C_2H_5$ | H | $C_2H_5$ |
| 7.34 | H | Br | $C_3H_7$ | H | $C_2H_5$ |
| 7.35 | 5-Cl | Br | H | H | $C_2H_5$ |
| 7.36 | 5-$CH_3$ | Br | H | H | $C_2H_5$ |
| 7.37 | H | Br | H | $CH_3$ | $C_2H_5$ |
| 7.38 | H | Br | H | $C_2H_5$ | $C_2H_5$ |
| 7.39 | H | Br | H | $C_2H_5$ | $C_2H_5$ |
| 7.40 | H | Br | H | S—$C_6H_5$ | $C_2H_5$ |
| 7.41 | H | Br | H | S—$C_6H_4$-4-Cl | $C_2H_5$ |
| 7.42 | H | Br | H | S—$C_6H_4$-4-Br | $C_2H_5$ |
| 7.43 | R | Br | H | S—$C_6H_4$-4-$CH_3$ | $C_2H_5$ |
| 7.44 | H | Br | H | S—$C_6H_4$-2-Cl | $C_2H_5$ |
| 7.45 | H | Br | H | S(=O)—$C_6H_5$ | $C_2H_5$ |
| 7.46 | H | Br | H | S(=O)$_2$—$C_6H_5$ | $C_2H_5$ |
| 7.47 | H | Br | H | $COCOOCH_3$ | $C_2H_5$ |
| 7.48 | H | Br | H | $COCOOC_2H_5$ | $CH_3$ |
| 7.49 | H | Br | H | $COCOOC_2H_5$ | $C_2H_5$ |
| 7.50 | H | Br | H | $COCON(C_2H_5)_2$ | $C_2H_5$ |
| 7.51 | H | Br | H | $COC_2H_5$ | $CH_3$ |
| 7.52 | H | Br | H | $COCH_3$ | $C_2H_5$ |
| 7.53 | H | Br | H | $COC_2H_5$ | $C_2H_5$ |
| 7.54 | H | Br | H | CO-i-$C_3H_7$ | $C_2H_5$ |
| 7.55 | H | Br | H | CO-c-$C_3H_5$ | $C_2H_5$ |
| 7.56 | H | Br | H | $COOCH_3$ | $C_2H_5$ |
| 7.57 | H | Br | H | $COOC_2H_5$ | $C_2H_5$ |
| 7.58 | 5-$CH_3$ | Cl | H | H | $C_2H_5$ |
| 7.59 | 5-Cl | Cl | H | H | $C_2H_5$ |
| 7.60 | H | Cl | $CH_3$ | H | $C_2H_5$ |
| 7.61 | H | Cl | $C_2H_5$ | H | $C_2H_5$ |
| 7.62 | H | Cl | H | $CH_3$ | $C_2H_5$ |
| 7.63 | H | Cl | H | $C_2H_5$ | $C_2H_5$ |
| 7.64 | H | Cl | H | i-$C_3H_7$ | $C_2H_5$ |
| 7.65 | H | Cl | H | $C_3H_7$ | $C_2H_5$ |
| 7.66 | H | Cl | H | S—$C_6H_5$ | $CH_3$ |
| 7.67 | H | Cl | H | S—$C_6H_5$ | $C_2H_5$ |
| 7.68 | H | Cl | H | S—$C_6H_4$-4-Cl | $C_2H_5$ |
| 7.69 | H | Cl | H | S—$C_6H_4$-4-Br | $C_2H_5$ |
| 7.70 | H | Cl | H | S—$C_6H_4$-4-$CH_3$ | $C_2H_5$ |
| 7.71 | H | Cl | H | S(=O)-$C_6H_5$ | $C_2H_5$ |
| 7.72 | H | Cl | H | S(=O)$_2$-$C_6H_5$ | $C_2H_5$ |
| 7.73 | H | Cl | H | $COCOOC_2H_5$ | $CH_3$ |
| 7.74 | H | Cl | H | $COCOOCH_3$ | $C_2H_5$ |
| 7.75 | H | Cl | H | $COCOOC_2H_5$ | $C_2H_5$ |
| 7.76 | H | Cl | H | $COCON(CH_3)_2$ | $C_2H_5$ |
| 7.77 | H | Cl | H | $COCON(C_2H_5)_2$ | $C_2H_5$ |
| 7.78 | H | Cl | H | $COCON(C_4H_9)_2$ | $C_2H_5$ |
| 7.79 | H | Cl | H | $COC_2H_5$ | $CH_3$ |
| 7.80 | H | Cl | H | $COCH_3$ | $C_2H_5$ |
| 7.81 | H | Cl | H | $COC_2H_5$ | $C_2H_5$ |
| 7.82 | H | Cl | H | CO-i-$C_3H_7$ | $C_2H_5$ |
| 7.83 | H | Cl | H | CO-c-$C_3H_5$ | $C_2H_5$ |

TABLE 7-continued

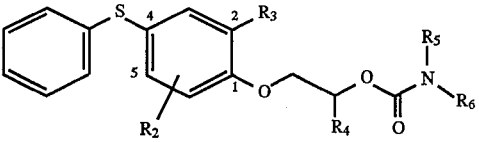

| Compounds | R₂ | R₃ | R₄ | R₅ | R₆ |
|---|---|---|---|---|---|
| 7.84 | H | Cl | H | COOCH₃ | C₂H₅ |
| 7.85 | H | Cl | H | COOC₂H₅ | C₂H₅ |
| 7.86 | H | Cl | H | COOC₃H₇ | C₂H₅ |
| 7.87 | H | Cl | H | COCOOC₈H₁₇ | C₂H₅ |
| 7.88 | H | Cl | H | COC₃H₇ | C₂H₅ |
| 7.89 | H | Cl | H | CO-c-C₅H₉ | C₂H₅ |
| 7.90 | H | CH₃ | H | H | CH₃ |
| 7.91 | H | CH₃ | H | H | C₂H₅ |
| 7.92 | H | CH₃ | H | H | CH₂CH₂Cl |
| 7.93 | H | CH₃ | H | H | CHClCH₃ |
| 7.94 | H | CH₃ | H | H | CH₂CH₂F |
| 7.95 | H | CH₃ | H | H | C₃H₇ |
| 7.96 | H | CH₃ | H | H | i-C₃H₇ |
| 7.97 | H | Cl | H | H | trans-CH₂CH=CHCH₃ |
| 7.98 | H | CH₃ | CH₃ | H | C₂H₅ |
| 7.99 | H | CH₃ | H | CH₃ | C₂H₅ |
| 7.100 | H | CH₃ | H | C₂H₅ | C₂H₅ |
| 7.101 | H | CH₃ | H | S—C₆H₅ | C₂H₅ |
| 7.102 | H | CH₃ | H | S—C₆H₄-4-Cl | C₂H₅ |
| 7.103 | H | CH₃ | H | S—C₆H₄-4-Br | C₂H₅ |
| 7.104 | H | CH₃ | H | S—C₆H₄-4-CH₃ | C₂H₅ |
| 7.105 | H | CH₃ | H | S—C₆H₄-2-Cl | C₂H₅ |
| 7.106 | H | CH₃ | H | COCOOCH₃ | C₂H₅ |
| 7.107 | H | CH₃ | H | COCOOC₂H₅ | C₂H₅ |
| 7.108 | H | CH₃ | H | COCON(C₂H₅)₂ | C₂H₅ |
| 7.109 | H | CH₃ | H | COCH₃ | C₂H₅ |
| 7.110 | H | CH₃ | H | COC₂H₅ | C₂H₅ |
| 7.111 | H | CH₃ | H | COC₃H₇ | C₂H₅ |
| 7.112 | H | CH₃ | H | CO-i-C₃H₇ | C₂H₅ |
| 7.1.13 | H | CH₃ | H | CO-c-C₃H₅ | C₂H₅ |
| 7.114 | H | Cl | H | H | C₆H₁₃ |
| 7.115 | 5-CH₃ | CH₃ | H | H | C₂H₅ |
| 7.116 | 5-Cl | CH₃ | H | H | C₂H₅ |
| 7.117 | H | Cl | H | COC₄H₉ | C₂H₅ |
| 7.118 | H | Cl | H | COOC₄H₉ | C₂H₅ |
| 7.119 | H | Cl | H | S—N(CH₃)COOC₄H₉ | C₂H₅ |
| 7.120 | H | CH₃ | H | C₄H₉ | C₂H₅ |

TABLE 8

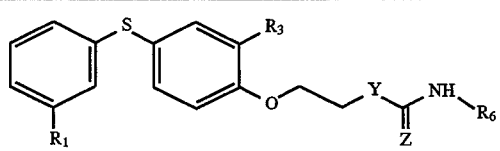

| Compounds | R₁ | R₃ | R₆ | Y | Z |
|---|---|---|---|---|---|
| 8.1 | H | CH₃ | C₂H₅ | S | O |
| 8.2 | H | Cl | C₂H₅ | S | O |
| 8.3 | H | Cl | C₂H₅ | O | S |
| 8.4 | H | Cl | C₂H₅ | S | S |
| 8.5 | H | Cl | CH₃ | O | S |
| 8.6 | H | CH₃ | C₂H₅ | O | S |
| 8.7 | H | Br | CH₃ | O | S |
| 8.8 | H | Br | C₂H₅ | O | S |
| 8.9 | Cl | Cl | C₂H₅ | O | S |
| 8.10 | Cl | Cl | CH₂CH=CH₂ | O | S |

TABLE 9

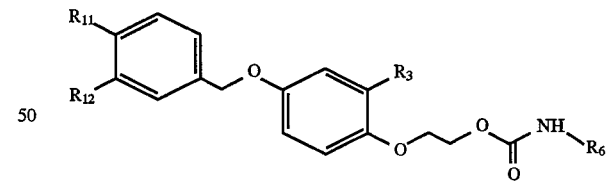

| Compounds | R₁₁ | R₁₂ | R₃ | R₆ |
|---|---|---|---|---|
| 9.1 | H | H | CH₃ | C₂H₅ |
| 9.2 | H | H | Cl | C₂H₅ |
| 9.3 | H | Cl | Cl | C₂H₅ |
| 9.4 | H | F | Cl | C₂H₅ |
| 9.5 | H | H | Cl | CH₃ |
| 9.6 | H | Cl | CH₃ | C₂H₅ |
| 9.7 | H | H | Br | CH₃ |
| 9.8 | H | H | Br | C₂H₅ |
| 9.9 | Cl | H | Cl | C₂H₅ |
| 9.10 | Cl | H | Cl | CH₂CH=CH₂ |
| 9.11 | H | H | F | C₂H₅ |

TABLE 10

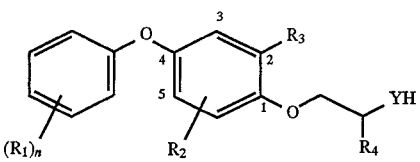

| Compounds | R₂ | R₃ | R₄ | Y |
|---|---|---|---|---|
| 10.1.1-26 | H | Cl | H | O |
| 10.2.1-26 | H | Br | H | O |
| 10.3.1-26 | H | Br | CH₃ | O |
| 10.4.1-26 | H | Br | C₂H₅ | O |
| 10.5.1-26 | H | Br | C₃H₇ | O |
| 10.6.1-26 | 5-Cl | Br | H | O |
| 10.7.1-26 | 5-CH₃ | Br | H | O |
| 10.8.1-26 | 5-CH₃ | Cl | H | O |
| 10.9.1-26 | 5-Cl | Cl | H | O |
| 10.10.1-26 | H | Cl | CH₃ | O |
| 10.11.1-26 | H | Cl | C₂H₅ | O |
| 10.12.1-26 | H | CH₃ | H | O |
| 10.13.1-26 | H | CH₃ | CH₃ | O |
| 10.14.1-26 | 5-CH₃ | CH₃ | H | O |
| 10.15.1-26 | 5-Cl | CH₃ | H | O |
| 10.16.1-26 | H | CH₃ | H | S |
| 10.17.1-26 | H | Cl | H | S |
| 10.18.2-26 | H | F | H | O |

TABLE 11

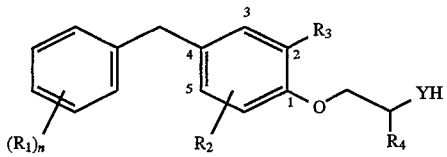

| Compounds | R₂ | R₃ | R₄ | Y |
|---|---|---|---|---|
| 11.1.1-7 | H | Cl | H | O |
| 11.2.1-7 | H | Br | H | O |
| 11.3.1-7 | H | Br | CH₃ | O |
| 11.4.1-7 | H | Br | C₂H₅ | O |
| 11.5.1-7 | H | Br | C₃H₇ | O |
| 11.6.1-7 | 5-Cl | Br | H | O |
| 11.7.1-7 | 5-CH₃ | Br | H | O |
| 11.8.1-7 | 5-CH | Cl | H | O |
| 11.9.1-7 | 5-Cl | Cl | H | O |
| 11.10.1-7 | H | Cl | CH₃ | O |
| 11.11.1-7 | H | Cl | C₂H₅ | O |
| 11.12.1-7 | H | CH₃ | H | O |
| 11.13.1-7 | H | CH₃ | CH₃ | O |
| 11.14.1-7 | 5-CH₃ | CH₃ | H | O |
| 11.15.1-7 | 5-Cl | CH₃ | H | O |
| 11.16.1-7 | H | CH₃ | H | S |
| 11.17.1-7 | H | Cl | H | S |
| 11.18.1-7 | H | F | H | O |

TABLE 12

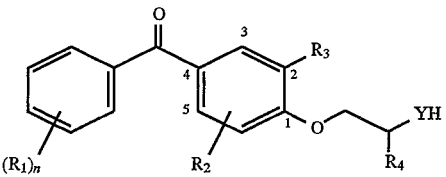

| Compounds | R₂ | R₃ | R₄ | Y |
|---|---|---|---|---|
| 12.1.1-2 | H | Cl | H | O |
| 12.2.1-2 | H | Br | H | O |
| 12.3.1-2 | H | Br | CH₃ | O |
| 12.4.1-2 | H | Br | C₂H₅ | O |
| 12.5.1-2 | H | Br | C₃H₇ | O |
| 12.6.1-2 | 5-Cl | Br | H | O |
| 12.7.1-2 | 5-CH₃ | Br | H | O |
| 12.8.1-2 | 5-CH₃ | Cl | H | O |
| 12.9.1-2 | 5-Cl | Cl | H | O |
| 12.10.1-2 | H | Cl | CH₃ | O |
| 12.11.1-2 | H | Cl | C₂H₅ | O |
| 12.12.1-2 | H | CH₃ | H | O |
| 12.13.1-2 | H | CH₃ | CH₃ | O |
| 12.14.1-2 | 5-CH₃ | CH₃ | H | O |
| 12.15.1-2 | 5-Cl | CH₃ | H | O |
| 12.16.1-2 | H | CH₃ | H | S |
| 12.17.1-2 | H | Cl | H | S |

TABLE 13

| Compounds | R₂ | R₃ | R₄ | Y |
|---|---|---|---|---|
| 13.1 | H | Cl | H | O |
| 13.2 | H | Br | H | O |
| 13.3 | H | Br | CH₃ | O |
| 13.4 | H | Br | C₂H₅ | O |
| 13.5 | H | Br | C₃H₇ | O |
| 13.6 | 5-Cl | Br | H | O |
| 13.7 | 5-CH₃ | Br | H | O |
| 13.8 | 5-CH₃ | Cl | H | O |
| 13.9 | 5-Cl | Cl | H | O |
| 13.10 | H | Cl | CH₃ | O |
| 13.11 | H | Cl | C₂H₅ | O |
| 13.12 | H | CH₃ | H | O |
| 13.13 | H | CH₃ | CH₃ | O |
| 13.14 | 5-CH₃ | CH₃ | H | O |
| 13.15 | 5-Cl | CH₃ | H | O |
| 13.16 | H | CH₃ | H | S |
| 13.17 | H | Cl | H | S |

TABLE 14

| Compound No. | Physical data (m.p. °C./$n_D^{20}$) |
|---|---|
| 1.1.6 | 106–107 |
| 1.2.1 | 47–48 |
| 1.2.3 | 64–65 |
| 1.2.4 | 42–43 |
| 1.2.5 | 63–64 |
| 1.2.6 | 73–74 |
| 1.2.7 | 65–66 |
| 1.3.6 | 58–59 |
| 1.5.6 | 54–55 |
| 1.9.1 | $n_D^{20} = 1.5742$ |

TABLE 14-continued

| Compound No. | Physical data (m.p. °C/$n_D^{20}$) |
|---|---|
| 1.9.7 | 57–58 |
| 1.11.1 | 54–55 |
| 1.12.1 | 83–84 |
| 1.21.1 | 75–76 |
| 1.22.1 | $n_D^{20}$ = 1.5618 |
| 1.26.3 | 67–68 |
| 1.68.6 | $n_D^{20}$ = 1.6209 |
| 1.75.6 | $n_D^{20}$ = 1.5441 |
| 1.80.6 | $n_D^{20}$ = 1.5640 |
| 1.91.1 | $n_D^{20}$ = 1.5501 |
| 1.91.4 | $n_D^{20}$ = 1.5521 |
| 1.121.1 | 79–81 |
| 1.122.1 | 55–56.5 |
| 1.124.1 | 155–155.5 |
| 1.125.1 | 67–68 |
| 1.126.1 | $n_D^{20}$ = 1.5541 |
| 1.127.3 | 79–80 |
| 1.180.6 | $n_D^{20}$ = 1.5586 |
| 1.181.1 | $n_D^{20}$ = 1.5428 |
| 2.2.6 | 76–78 |
| 2.3.6 | $n_D^{20}$ = 1.6071 |
| 2.9.6 | $n_D^{20}$ = 1.6109 |
| 3.1.1 | 74–75 |
| 3.2.1 | 68–70 |
| 3.2.4 | 93–95 |
| 3.2.6 | 102–103 |
| 3.2.7 | 120–121 |
| 3.26.1 | 78–79 |
| 3.26.3 | 67–68 |
| 5.2.1 | 113–114 |
| 5.9.1 | 111–112 |
| 9.2 | 48–49 |
| 10.1.1 | $n_D^{20}$ = 1.5929 |
| 10.1.3 | $n_D^{20}$ = 1.5776 |
| 10.1.4 | $n_D^{20}$ = 1.5761 |
| 10.1.5 | $n_D^{20}$ = 1.5631 |
| 10.1.6 | $n_D^{20}$ = 1.5995 |
| 10.1.7 | $n_D^{20}$ = 1.6019 |
| 10.10.6 | $n_D^{20}$ = 1.5819 |
| 10.12.1 | 55–56 |
| 10.18.1 | $n_D^{20}$ = 1.5586 |
| 11.1.1 | 65–66.5 |
| 11.1.7 | 91–92 |
| 11.2.1 | 72–73 |
| 11.2.3 | $n_D^{20}$ = 1.5902 |
| 11.18.3 | $n_D^{20}$ = 1.5548 |
| 12.1.1 | 88–89 |

Formulation examples (% = percent by weight)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Petroleum spirit (boiling range 160–190° C.) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly-disperse silica | 1% | — | 13% | 7% |
| Attapulgite | — | 90% | — | 18% |

The active ingredient is dissolved in dichloromethane, the solution is sprayed onto the carrier, and the solvent is subsequently evaporated in vacuo.

| Example F4: Dusts | a) | b) |
|---|---|---|
| Active ingredient | 2% | 5% |
| Highly-disperse silica | 1% | 5% |
| Talc | 97% | — |
| Kaolin | — | 90% |

Ready-to-use dusts are obtained by intimately mixing the carriers with the active ingredient.

| Example F5: Wettable powders | a) | b) | c) |
|---|---|---|---|
| Active ingredient | 25% | 50% | 75% |
| Sodium ligninsulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 mol of EO) | — | 2% | — |
| Highly-disperse silica | 5% | 10% | 10% |
| Kaolin | 62% | 27% | — |

The active ingredient is mixed with the additives and the mixture is ground thoroughly in a suitable mill. This gives wettable powders which can be diluted with water to give suspensions of any desired concentration.

| Example F6: Emulsion concentrate | |
|---|---|
| Active ingredient | 10% |
| Octylphenol polyethylene glycol ether (4–5 mol of EO) | 3% |
| Calcium dodecylbenzenesulfonate | 3% |
| Castor oil polyglycol ether (36 mol of EO) | 4% |
| Cyclohexanone | 30% |
| Xylene mixture | 50% |

Emulsions of any desired concentration can be prepared from this concentrate by dilution with water.

| Example F7: Dusts | a) | b) |
|---|---|---|
| Active ingredient | 5% | 8% |
| Talc | 95% | — |
| Kaolin | — | 92% |

Ready-to-use dusts are obtained by mixing the active ingredient with the carrier and grinding the mixture in a suitable mill.

| Example F8: Extruder granules | |
|---|---|
| Active ingredient | 10% |
| Sodium ligninsulfonate | 2% |
| Carboxymethylcellulose | 1% |
| Kaolin | 87% |

-continued

The active ingredient is mixed with the additives and the mixture is ground and moistened with water. This mixture is extruded, granulated and subsequently dried in a stream of air.

Example F9: Coated granules

| Active ingredient | 3% |
|---|---|
| Polyethylene glycol (MW 200) | 3% |
| Kaolin | 94% |

In a mixer, the finely ground active ingredient is applied uniformly to the kaolin which has been moistened with polyethylene glycol. Dust-free coated granules are obtained in this manner.

Example F10: Suspension concentrate

| Active ingredient | 40% |
|---|---|
| Ethylene glycol | 10% |
| Nonylphenol polyethylene glycol ether (15 mol of EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is mixed intimately with the additives. This gives a suspension concentrate from which suspensions of any desired concentration can be prepared by dilution with water.

Biological examples (%=per cent by weight, unless stated otherwise)

A. Insecticidal activity

EXAMPLE B1

Activity against *Adoxophyes reticulana* (ovicidal)

*Adoxophyes reticulana* eggs which have been deposited on filter paper are briefly immersed into a test solution comprising 400 ppm of active ingredient in acetone/water. After the test solution has dried on, the eggs are incubated in Petri dishes. After 6 days, the hatching percentage of the eggs is evaluated by comparison with untreated control batches (% reduction in hatching rate).

In this test, a good activity is exhibited by compounds of Tables 1 to 9 and 14. An activity of over 80 % is exhibited, in particular, by Compounds No. 1.2.1, 1.2.3 and 1.2.6.

EXAMPLE B2

Activity against *Aonidiella aurantii*

Potato tubers are populated with *Aonidiella aurantii* crawlers. After about 2 weeks, the potatoes am immersed into an aqueous emulsion spray mixture, or suspension spray mixture, comprising 400 ppm of active ingredient. After the tubers have dried, they are incubated in a plastic container. To evaluate the experiment, the survival rate of the crawlers of the first subsequent generation of the treated population is compared 10 to 12 weeks later with that of untreated control batches.

In this test, a good activity is exhibited by compounds of Tables 1 to 9 and 14. An activity of over 80 % is exhibited, in particular, by Compounds No. 1.2.1, 1.2.3 and 1.2.6.

EXAMPLE B3

Activity against *Bemisia tabaci*

Dwarf bean plants are placed under gauze cages and populated with *Bemisia tabaci* adults. After oviposition has taken place, all adults are removed. 10 days later, the plants with the nymphs are sprayed with an aqueous emulsion spray mixture comprising 400 ppm of active ingredient. After a further 14 days, the hatching percentage of the eggs is evaluated by comparison with untreated control batches.

In this test, a good activity is exhibited by compounds of Tables 1 to 9 and 14. An activity of over 80 % is exhibited, in particular, by Compounds No. 1.2.1, 1.2.3 and 1.2.6.

EXAMPLE B4

Activity against *Bemisia tabaci*

Dwarf bean plants are placed under gauze cages and populated with *Bemisia tabaci* adults. After oviposition has taken place, all adults are removed. 2 days later, the plants with the nymphs are sprayed with an aqueous emulsion spray mixture comprising 400 ppm of active ingredient. After a further 14 days, the hatching percentage of the eggs is evaluated by comparison with untreated control batches.

In this test, a good activity is exhibited by compounds of Tables 1 to 9 and 14. An activity of over 80 % is exhibited, in particular, by Compounds No. 1.2.1, 1.2.3, 1.2.4, 1.2.6, 1.2.7, 3.1.1 and 3.26.3.

EXAMPLE B5

Activity against *Cydia pomonella* (ovicidal)

*Cydia pomonella* eggs which have been deposited on filter paper are briefly immersed into a test solution comprising 400 ppm of active ingredient in acetone/water. After the test solution has dried on, the eggs are incubated in Petri dishes. After 6 days, the hatching percentage of the eggs is evaluated by comparison with untreated control batches (% reduction in hatching rate).

In this test, a good activity is exhibited by compounds of Tables 1 to 9 and 14. An activity of over 80 % is exhibited, in particular, by Compounds No. 1.2.1, 1.2.3 and 1.2.6.

EXAMPLE B6

Activity against *Diabrotica balteata* (ovicidal)

20 to 50 *Diabrotica balteata* eggs which have been deposited on a filter cloth are transferred to a Petri dish and treated with an aqueous emulsion spray mixture comprising 400 ppm of active ingredient. The Petri dish is incubated at 24°. After 7 days, the hatching percentage of the eggs is evaluated by comparison with untreated control batches (% reduction in hatching rate).

In this test, a good activity is exhibited by compounds of Tables 1 to 9 and 14.

EXAMPLE B7

Activity against *Heliothis virescens* (ovi/larvicidal)

*Heliothis virescens* eggs which have been deposited on cotton are sprayed with an aqueous emulsion spray mixture comprising 400 ppm of active ingredient. After 8 days, the hatching percentage of the eggs and the survival rates of the caterpillars are evaluated by comparison with untreated control batches (% reduction in population).

In this test, a good activity is exhibited by compounds of Tables 1 to 9 and 14. An activity of over 80 % is exhibited, in particular, by Compounds No. 1.2.1, 1.2.3, 1.2.4, 1.2.5, 1.2.6, 1.26.3 and 3.26.3.

EXAMPLE B8

Activity against *Heliothis virescens* (ovicidal)

*Heliothis virescens* eggs which have been deposited on filter paper are briefly immersed into a test solution comprising 400 ppm of active ingredient in acetone/water. After the test solution has dried on, the eggs are incubated in Petri dishes. After 6 days, the hatching percentage of the eggs is evaluated by comparison with untreated control batches (% reduction in hatching rate).

In this test, a good activity is exhibited by compounds of Tables 1 to 9 and 14. An activity of over 80 % is exhibited, in particular, by Compounds No. 1.1.6, 1.2.1, 1.2.3, 1.2.4, 1.2.5, 1.2.6, 1.26.3, 1.3.6, 1.9.1, 2.2.6, 2.9.6, 3.26.3, 5.2.1 and 5.9.1.

EXAMPLE B9

Activity against *Lobesia botrana* (ovicidal)

*Lobesia botrana* eggs which have been deposited on filter paper are briefly immersed into a test solution comprising 400 ppm of active ingredient in acetone/water. After the test solution has dried on, the eggs are incubated in Petri dishes. After 6 days, the hatching percentage of the eggs is evaluated by comparison with untreated control batches (% reduction in hatching rate).

In this test, a good activity is exhibited by compounds of Tables 1 to 9 and 14. An activity of over 80 % is exhibited, in particular, by Compounds No. 1.2.1, 1.2.3 and 1.2.6.

EXAMPLE B 10

Activity against *Nilaparvata lugens*

Rice plants are treated with an aqueous emulsion spray mixture comprising 400 ppm of active ingredient. After the spray coating has dried on, the rice plants are populated with plant hopper larvae in the 2nd and 3rd stages. The test is evaluated after 21 days. The percentage reduction in population (% activity) is determined by comparing the number of surviving plant hoppers on the treated and on untreated plants.

In this test, a good activity is exhibited by compounds of Tables 1 to 9 and 14. An activity of over 80 % is exhibited, in particular, by Compounds No. 1.2.1, 1.2.3 and 1.2.6.

B. Acaricidal activity

EXAMPLE B 11

Activity against Boophilus microplus

Adult female ticks which have sucked themselves full are glued onto a PVC plate and covered with a cotton wool ball. To treat the test animals, 10 ml of an aqueous test solution comprising 125 ppm of active ingredient is poured over them. The cotton wool ball is then removed and the ticks are incubated for 4 weeks for oviposition. The activity against *Boophilus microplus* manifests itself in the case of the females as mortality or sterility or in the case of the eggs as ovicidal activity.

In this test, a good activity is exhibited by compounds of Tables 1 to 9 and 14.

I claim:
1. A compound of the formula

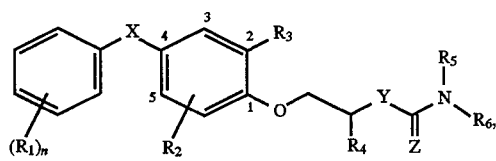

in which $R_1$ is halogen, $C_1$–$C_3$alkyl, halo-$C_1$–$C_3$alkyl, $C_1$–$C_3$alkoxy, halo-$C_1$–$C_3$alkoxy or cyano and/or two substituents $R_1$ which are bonded to adjacent C atoms of the phenyl ring together are —O—$CH_2$—O—;

$R_2$ is hydrogen, halogen or methyl;

$R_3$ is fluorine, chlorine, bromine or $C_1$–$C_3$alkyl;

$R_4$ is hydrogen or $C_2$–$C_3$alkyl;

either $R_5$ is hydrogen, $C_1$–$C_4$alkyl,

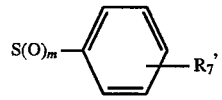

—COCO—$R_8$, —CO—$R_9$ or $S(O)_m$—$N(R_{10})$—COO—$R_{11}$ and $R_6$ is $C_1$–$C_4$alkyl, halo-$C_1$–$C_4$alkyl, $C_2$–$C_6$alkenyl, halo-$C_3$–$C_4$alkenyl, $C_3$–$C_5$alkynyl, halo-$C_3$–$C_5$alkynyl, $C_1$–$C_3$alkoxy,-$C_1$–$C_3$alkyl, $C_3$–$C_6$-cycloalkyl, unsubstituted phenyl or phenyl which is monosubstituted to trisubstituted by identical or different substituents selected from the group consisting of halogen, $C_1$–$C_4$alkyl and $C_1$–$C_4$alkoxy;

or $R_5$ and $R_6$ together are —$(CH_2)_4$— or —$(CH_2)_5$—;

$R_7$ is hydrogen, halogen or $C_1$–$C_3$alkyl;

$R_8$ is $C_2$–$C_8$alkoxy or —$N(R_{12})_2$;

$R_9$ is $C_2$–$C_4$alkyl, $C_3$–$C_6$cycloalkyl, —$N(R_{13})_2$ or $C_1$–$C_4$alkoxy;

$R_{10}$ is $C_1$–$C_3$alkyl;

$R_{11}$ is $C_1$–$C_6$alkyl;

$R_{12}$ radicals independently of one another are $C_2$–$C_8$alkyl;

$R_{13}$ radicals independently of one another are $C_2$–$C_4$alkyl;

m is the number 0, 1 or 2;

n is the number 0, 1, 2 or 3 where, if n is 2 or 3, the radicals $R_1$ can be identical or different;

X is O, S, $CH_2$, CO or —O—$CH_2$—;

Y is O or S; and

Z is O or S, with the exception of 1-(2-fluoro-4-phenoxyphenoxy)-2-ethylaminocarbonyloxyethane, in each case in free form or in salt form.

2. A compound according to claim 1 of the formula I in which $(R_1)_n$ is $(R_1)_0$, monofluoro, monochloro, monobromo, difluoro, dichloro, monochloromonofluoro, monobromomonofluoro, monomethyl, monoethyl, dimethyl, monomethoxy, monocyano, monotrifluoromethyl, monotrifluoromethoxy or monomethylenedioxy.

3. A compound according to claim 1 of the formula I in which $R_2$ is hydrogen, chlorine or methyl.

4. A compound according to claim 1 of the formula I in which $R_3$ is chlorine, bromine or methyl.

5. A compound according to claim 1 of the formula I in which $R_3$ is fluorine.

6. A compound according to claim 1 of the formula I in which $R_4$ is hydrogen.

7. A compound according to claim 1 of the formula I in which $R_5$ is hydrogen, $C_1$–$C_4$alkyl, —S—$C_6H_4$—Cl, —COCO—$R_8$, in which $R_8$ is $C_1$–$C_4$alkoxy, or —CO—$R_9$, in which $R_9$ is $C_1$–$C_4$alkyl, $C_1$–$C_4$alkoxy or $C_3$–$C_6$cycloalkyl.

8. A compound according to claim 1 of the formula I in which $R_6$ is $C_1$–$C_6$alkyl, halo-$C_1$–$C_3$alkyl, $C_2$–$C_4$alkenyl, halo-$C_3$–$C_4$alkenyl, $C_3$–$C_4$alkynyl, $C_1$–$C_2$alkoxy-$C_1$–$C_2$alkyl or $C_3$–$C_6$cycloalkyl.

9. A compound according to claim 1 of the formula I in which $R_5$ and $R_6$ together are —$(CH_2)_4$— or —$(CH_2)_5$—.

10. A compound according to claim 1 of the formula I in which X is O, $CH_2$, CO or —O—$CH_2$—.

11. A compound according to claim 1 of the formula I in which Y is O.

12. A compound according to claim 1 of the formula I in which Z is O.

13. A compound according to claim 1 of the formula I in which $(R_1)_n$ is $(R_1)_0$, 2-, 3- or 4-fluoro, 3- or 4-chloro, 4-bromo, 2,4- or 3,5-difluoro, 3,4- or 3,5-dichloro, 3-chloro-4-fluoro, 4-bromo-2-fluoro, 3- or 4-methyl, 3- or 4-ethyl, 3,5-dimethyl, 3- or 4-methoxy, 4-cyano, 3- or 4-trifluoromethyl, 3- or 4-trifluoromethoxy or 3,4-methylenedioxy, $R_2$ is hydrogen, chlorine or methyl, $R_3$ is fluorine, chlorine, bromine or methyl, $R_4$ is hydrogen, either $R_8$ is hydrogen, $C_1$–$C_4$alkyl,

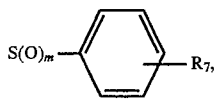

—COCO—$R_8$ or —CO—$R_9$ and $R_6$ is $C_1$–$C_6$alkyl, halo-$C_1$–$C_3$alkyl, $C_2$–$C_4$alkenyl, $C_3$–$C_4$alkynyl, $C_1$–$C_2$alkoxy-$C_1$–$C_2$alkyl or phenyl which is monosubstituted by halogen; or $R_5$ and $R_6$ together are —$(CH_2)_4$— or —$(CH_2)_5$—; X is O, $CH_2$, CO or —O—$CH_2$; Y is O or S, Z is O or S, $R_7$ is hydrogen or halogen; $R_8$ is $C_1C_4$alkoxy; $R_9$ is $C_1$–$C_4$alkyl or $C_3$–$C_6$cycloalkyl and m is 0 or 1.

14. A compound according to claim 13 of the formula I in which $(R_1)_n$, is $(R_1)_0$, 3- or 4-fluoro, 3-chloro, 3,5-difluoro or 3,4-dichloro, $R_2$ is hydrogen, $R_3$ is chlorine, $R_4$ is hydrogen, either $R_5$ is hydrogen and $R_6$ is $C_1$–$C_3$alkyl, halo-$C_1$–$C_2$alkyl, $C_2$–$C_4$alkenyl, $C_3$–$C_4$alkynyl, $C_1$–$C_2$alkoxy-$C_1$–$C_2$alkyl or phenyl which is monosubstituted by chlorine; or $R_5$ and $R_6$ together are —$(CH_2)_4$—; X is O, $CH_2$, CO or —O—$CH_2$—; Y is O or S and Z is O or S.

15. A compound according to claim 14 of the formula I in which $(R_1)_n$ is $(R_1)_0$, $R_2$ is hydrogen, $R_3$ is fluorine, $R_4$ is hydrogen, $R_5$ is hydrogen, $R_6$ is $C_1$–$C_3$alkyl and X, Y and Z are in each case O.

16. A compound according to claim 15 of the formula I in which $(R_1)_n$ is $(R_1)_0$, 3-chloro or 3,5-difluoro, $R_2$ is hydrogen, $R_3$ is chlorine, $R_4$ is hydrogen, $R_5$ is hydrogen, $R_6$ is $C_1$–$C_2$alkyl or chloro-$C_1$–$C_2$alkyl and X, Y and Z are in each case O.

17. A compound according to claim 1 of the formula I selected from the group of compounds consisting of
1-[2-chloro-4-(3-chlorophenoxy)phenoxy]-2-ethylaminocarbonyloxyethane,
1-(2-chloro-4-phenoxyphenoxy)-2-ethylaminocarbonyloxyethane and
1-[2-chloro-4-(3,5-difluorophenoxy)phenoxy]-2-ethylaminocarbonyloxyethane.

18. A pesticide which comprises at least one compound according to claim 1 of the formula I, with the exception of 1-(2-fluoro-4-phenoxyphenoxy)-2-ethylaminocarbonyloxyethane, in each case in free form or in agrochemically utilizable salt form, as active ingredient and, if desired, at least one auxiliary.

19. A composition according to claim 18 for controlling insects and representatives of the order Acarina.

* * * * *